(12) United States Patent
Siebers et al.

(10) Patent No.: US 11,850,448 B2
(45) Date of Patent: Dec. 26, 2023

(54) SYSTEM AND METHOD TO COMPUTE A PIXEL SENSITIVITY MAP OF AN IMAGING DEVICE

(71) Applicant: UNIVERSITY OF VIRGINIA PATENT FOUNDATION, Charlottesville, VA (US)

(72) Inventors: Jeffrey Vincent Siebers, Richmond, VA (US); Mahmoud Ahmed, Charlottesville, VA (US)

(73) Assignee: UNIVERSITY OF VIRGINIA PATENT FOUNDATION

( * ) Notice: Subject to any disclaimer, the term of this patent is extended or adjusted under 35 U.S.C. 154(b) by 15 days.

(21) Appl. No.: 18/065,727

(22) Filed: Dec. 14, 2022

(65) Prior Publication Data

US 2023/0110386 A1 Apr. 13, 2023

Related U.S. Application Data

(63) Continuation of application No. 17/336,697, filed on Jun. 2, 2021, now Pat. No. 11,565,133.

(Continued)

(51) Int. Cl.
*A61N 5/10* (2006.01)

(52) U.S. Cl.
CPC .... *A61N 5/1075* (2013.01); *A61N 2005/1054* (2013.01); *G06T 2207/10116* (2013.01)

(58) Field of Classification Search
None
See application file for complete search history.

(56) References Cited

U.S. PATENT DOCUMENTS

| 2009/0129659 A1* | 5/2009 | Deutschmann | ........ H04N 5/361 |
| | | | 250/252.1 |
| 2010/0046696 A1* | 2/2010 | Maltz | .................... G06T 11/005 |
| | | | 378/7 |

(Continued)

OTHER PUBLICATIONS

D. W. Bailey, L. Kumaraswamy, M. Bakhtiari, H. K. Malhotra, and M. B. Podgorsak, EPID dosimetry for pretreatment quality assurance with two commercial systems., Journal of applied clinical medical physics / American College of Medical Physics 13, 3736 (2012).

(Continued)

*Primary Examiner* — Hoon K Song
(74) *Attorney, Agent, or Firm* — Meunier Carlin & Curfman LLC

(57) ABSTRACT

An image calibration method includes capturing and correcting a flood field image for background signal and effects of known image-panel features (dead/bad pixels). The corrected image is processed to separate frequencies characteristic of relative pixel sensitivities from frequencies characteristic of radiation energy fluence. The incident energy fluence has a known maximum in-field energy fluence gradient. A model that describes the incident energy fluence on a detector is generated or received. The corrected image may be modeled at frequencies at or below the maximum in-field energy fluence gradient. A pixel sensitivity matrix (PSM) is generated by adjusting the corrected image with the model of the incident energy fluence on the detector. For example, the corrected image signal may be divided by the model or the model may be subtracted from the corrected image. The PSM may be used to correct additional raw images captured by the detector.

20 Claims, 14 Drawing Sheets

Related U.S. Application Data

(60) Provisional application No. 63/033,421, filed on Jun. 2, 2020.

(56) References Cited

U.S. PATENT DOCUMENTS

| | | | | |
|---|---|---|---|---|
| 2015/0352376 | A1* | 12/2015 | Wiggers | A61B 6/06 378/207 |
| 2017/0278277 | A1* | 9/2017 | Morf | A61B 6/032 |
| 2020/0206539 | A1* | 7/2020 | Han | A61N 5/1081 |

OTHER PUBLICATIONS

B. Mijnheer, I. Olaciregui-Ruiz, R. Rozendaal, J.-J. Sonke, H. Spreeuw, R. Tielenburg, M. v. Herk, R. Vijlbrief, and A. Mans, 3D EPID-based in vivo dosimetry for IMRT and VMAT, Journal of Physics: Conference Series 444, 012011 (2013).
H. C. Woodruff, T. Fuangrod, E. Van Uytven, B. M. C. McCurdy, T. Van Beek, S. Bhatia, P. B. Greer, E. V. Uytven, B. M. C. McCurdy, T. Van Beek, S. Bhatia, and P. B. Greer, First Experience with Real-Time EPID-Based Delivery Verification during IMRT and VMAT Sessions, International Journal of Radiation Oncology Biology Physics 93, 516-522 (2015).
M. Bakhtiari, L. Kumaraswamy, D. W. Bailey, S. De Boer, H. K. Malhotra, and M. B. Podgorsak, Using an EPID for patient-specific VMAT quality assurance, Medical Physics 38, 1366-1373 (2011).
J. A. Walker, The use of an on-board MV imager for plan verification of intensity modulated radiation therapy and volumetrically modulated arc therapy, (2013), 81 pages.
P. M. McCowan, G. Asuni, T. van Beek, E. van Uytven, K. Kujanpaa, and B. M. C. McCurdy, A model-based 3D patient-specific pre-treatment QA method for VMAT using the EPID, Physics in Medicine and Biology 62, 1600-1612 (2017).
L. S. Wootton, M. J. Nyflot, W. A. Chaovalitwongse, and E. Ford, Error Detection in Intensity-Modulated Radiation Therapy Quality Assurance Using Radiomic Analysis of Gamma Distributions, International Journal of Radiation Oncology Biology Physics 102, 219-228 (2018).
B. Neal, M. Ahmed, K. Kathuria, T. Watkins, K. Wijesooriya, and J. Siebers, A clinically observed discrepancy between image-based and log-based MLC positions, Medical Physics 43, 2933-2935 (2016).
H. Parsaei, E. El-Khatib, and R. Rajapakshe, The use of an electronic portal imaging system to measure portal dose and portal dose profiles, Medical Physics 25, 1903-1909 (1998).
P. B. Greer and C. C. Popescu, Dosimetric properties of an amorphous silicon electronic portal imaging device for verification of dynamic intensity modulated radiation therapy, Medical Physics 30, 1618-1627 (2003).
J. V. Siebers, J. O. Kim, L. Ko, P. J. Keall, and R. Mohan, Monte Carlo computation of dosimetric amorphous silicon electronic portal images, Medical Physics 31, 2135-2146 (2004).
A. Van Esch, T. Depuydt, and D. P. Huyskens, The use of an aSi-based EPID for routine absolute dosimetric pre-treatment verification of dynamic IMRT fields, Radiotherapy and Oncology 71, 223-234 (2004).
P. B. Greer, Correction of pixel sensitivity variation and off-axis response for amorphous silicon EPID dosimetry, Medical Physics 32, 3558-3568 (2005).
L. Parent, A. L. Fielding, D. R. Dance, J. Seco, and P. M. Evans, Amorphous silicon EPID calibration for dosimetric applications: comparison of a method based on Monte Carlo prediction of response with existing techniques, Physics in Medicine and Biology 52, 3351-3368 (2007).
L. Parent, J. Seco, P. M. Evans, A. Fielding, and D. R. Dance, Monte Carlo modelling of a-Si EPID response: The effectof spectral variations with field size and position, Medical Physics 33, 4527-4540 (2006).
B. Cai, S. M. Goddu, S. Yaddanapudi, D. Caruthers, J. Wen, C. Noel, S. Mutic, and B. Sun, Normalize the response of EPID in pursuit of linear accelerator dosimetry standardization, Journal of Applied Clinical Medical Physics 19, 73-85 (2018).
T. A. Simon, W. E. Simon, D. Kahler, J. Li, and C. Liu, Wide field array calibration dependence on the stability of measured dose distributions, Medical Physics 37, 3501-3509 (2010).
L. E. Antonuk, J. Yorkston, W. Huang, H. Sandler, J. H. Siewerdsen, and Y. El-Mohri, Megavoltage imaging with a large-area, flat-panel, amorphous silicon imager, International Journal of Radiation Oncology Biology Physics 36, 661-672 (1996).
L. E. Antonuk, Electronic portal imaging devices: A review and historical perspective of contemporary technologies and research, Physics in Medicine and Biology 47 R31-R65 (2002).
M. Ahmad, H. Nourzadeh, B. Neal, W. Watkins, and J. Siebers, A Fast Yet Sensitive EPID-Based Real-Time Treatment Verification System, Medical Physics 43, 3711-3712 (2016).
Ahmed, M., Nourzadeh, H., Brian, A., Watkins, W., Siebers, J., EPID-Based Real-Time Patient Misalignment Detection Algorithm: TH-AB-FS1-06, Medical physics. vol. 44 (2017).
H. C. Woodruff and P. B. Greer, 3D Dose reconstruction: Banding artefacts in cine mode EPID images during VMAT delivery, Journal of Physics: Conference Series 444, 012042 (2013).
Varian Medical Systems, TrueBeam Technical Reference Guide—vol. 2: Imaging, vol. 2, (2013). https://www.varian.com/products/radiotherapy/treatment-delivery/truebeam.
M. Alshanqity and A. Nisbet, Dosimetric Performance of A-Si Electronic Portal Imaging Devices, International Journal of Medical Physics, Clinical Engineering and Radiation Oncology 05, 162-175 (2016).
S. Wang, J. K. Gardner, J. J. Gordon, W. Li, L. Clews, P. B. Greer, and J. V. Siebers, Monte Carlo-based adaptive EPID dose kernel accounting for different field size responses of imagers, Medical Physics 36, 3582-3595 (2009).
L. Ko, J. O. Kim, and J. V. Siebers, Investigation of the optimal backscatter for an aSi electronic portal imaging device, Physics in Medicine and Biology 49, 1723 (2004).
A. Boriano, F. Lucio, E. Calamia, E. Russi, and F. Marchetto, A new approach for the pixel map sensitivity (PMS) evaluation of an electronic portal imaging device (EPID), Journal of Applied Clinical Medical Physics 14, 234-250 (2013).
B. Sun, S. Yaddanapudi, S. M. Goddu, and S. Mutic, A self-sufficient method for calibration of Varian electronic portal imaging device, Journal of Physics: Conference Series 573, 012041 (2015).
D. L'etourneau, M. Gulam, D. Yan, M. Oldham, and J. W. Wong, Evaluation of a 2D diode array for IMRT quality assurance, in Radiotherapy and Oncology 70, 199-206 (2004).
E. Klein, J. Hanley, J. Bayouth, F. Yin, W. Simon, S. Dresser, C. Serago, Task Group 142 report: Quality assurance of medical accelerators, in Medical Physics 36, 4197-4212 (2009).
M. Miften, A. Olch, D. Mihailidis, J. Moran, T. Pawlicki, A. Molineu, H. Li, K. Wijesooriya, J. Shi, P. Xia, N. Papanikolaou, D. Low, Tolerance limits and methodologies for IMRT measurement-based verication QA: Recommendations of AAPM Task Group No. 218, in Medical Physics 45, e53-e83 (2018).
J. Moore and J. V. Siebers, Verification of the optimal backscatter for an a-Si electronic portal imaging device, Physics in Medicine and Biology 50, 2341-2350 (2005).
P. Rowshanfarzad, B. McCurdy, M. Sabet, C. Lee, D. O'Connor and B. Greer, Measurement and modeling of the effect of support arm backscatter on dosimetry with a Varian EPID, Physics in Medicine and Biology 37, 2269-2278 (2010).
P. Greer, P. Cadman, C. Lee, and K. Bzdusek, An energy fluence-convolution model for amorphous silicon EPID dose prediction, Medical Physics 36, 547-555 (2009).
J. Siebers, I. Popescud and R. Berbeco. "Monte Carlo Simulation of EPIDs". In Beam's Eye View Imaging in Radiation Oncology. CRC Press. 19 pages (2017).

* cited by examiner

SYSTEM AND METHOD TO COMPUTE A PIXEL SENSITIVITY MAP OF AN IMAGING DEVICE

BACKGROUND

Radiation dosimetry and verification are key components of today's work-flow of oncology clinics. With the current advancements in dose delivery techniques, comes the need for comprehensive quality assurance (QA) procedures to ensure patient and staff safety. Electronic portal imaging devices (EPIDs) have been playing an increasing role in pre- and during treatment quality assurance since they come pre-mounted on most linear accelerators and have high spatial resolution. Moreover, an EPID can be easily integrated into the clinical workflow, its signal readout can provide real-time feedback, and it can be deployed during treatment for transmission dosimetry. The EPID can capture exit-fluence radiation as cine images in the beam eye-view, which makes them ideal for transit dose QA and analysis of complex deliveries.

EPIDs were initially designed as imaging panels; flood-field calibrations were utilized to normalize inherent pixel-to-pixel sensitivity variations to a resultant flat image. To use EPIDs as proper dosimeter, the relative pixel sensitivities need to preserve the dosimetric integrity of the input beam, including the off-axis beam profile. Methods of determining the pixel sensitivity matrix (PSM) which converts the EPID raw signal to a dosimetric response have been previously reported, including using thick phantoms and large distances to create a dosimetrically flat field, apply off-axis pixel response corrections and methods which cross-correlate pixel responses from multiple measurements made while shifting the EPID with respect to a fixed radiation field.

SUMMARY

A first aspect of the disclosure provides an image calibration method. The image calibration method comprises capturing a flood field signal with an image detector from incident energy fluence produced by a signal source. The method comprises separating frequency components of the flood field signal into frequency components characteristic of variations in the incident energy fluence and frequency components characteristic of pixel-to-pixel sensitivity variations of the image detector. The method comprises determining a pixel sensitivity matrix from the flood field signal and the frequency components characteristic of variations in the incident energy fluence.

In some implementations of the first aspect of the disclosure, separating frequency components of the flood field signal comprises generating a fluence-signal-fitted model that models the frequency components characteristic of variations in the incident energy fluence.

In some implementations of the first aspect of the disclosure, the fluence-signal-fitted model has a frequency cut-off characteristic of topological properties of the incident energy fluence.

In some implementations of the first aspect of the disclosure, the frequency cut-off is a maximum in-field energy fluence gradient of the incident energy fluence.

In some implementations of the first aspect of the disclosure, the fluence-signal-fitted model is a surface-fit polynomial model, a surface fitting model, a regional-surface fitting model, a weighted-surface fitting model, a signal smoothing model, a low-pass filter model, a signal frequency decomposition model, a Fourier analysis model, or an image denoising model.

In some implementations of the first aspect of the disclosure, the fluence-signal-fitted model satisfies a condition that a derivative of an incident energy fluence integral with respect to the fluence-signal-fitted model is minimized.

In some implementations of the first aspect of the disclosure, the method further comprises correcting the flood field signal for background dark-field and/or bad pixels to produce a corrected image signal.

In some implementations of the first aspect of the disclosure, determining the pixel sensitivity matrix comprises adjusting the corrected image signal based on the fluence-signal-fitted model. For example, the corrected image signal may be divided by the fluence-signal-fitted model. In another example, the fluence-signal-fitted model may be subtracted from the corrected image signal. Other adjustments to the corrected image signal based on the fluence-signal-fitted model are contemplated.

In some implementations of the first aspect of the disclosure, the method further comprises capturing an image with the image detector of an object irradiated by energy fluence produced by the signal source and correcting the image of the object using the pixel sensitivity matrix.

In some implementations of the first aspect of the disclosure, the image detector is an electronic portal imaging device.

A second aspect of the disclosure provides an imaging system. The imaging system comprises a signal source, an image detector, and a controller configured to calibrate the image detector. The controller is configured to capture a flood field signal with an image detector from incident energy fluence produced by a signal source. The controller is further configured to separate frequency components of the flood field signal into frequency components characteristic of variations in the incident energy fluence and frequency components characteristic of pixel-to-pixel sensitivity variations of the image detector. The controller is further configured to determine a pixel sensitivity matrix from the flood field signal and the frequency components characteristic of variations in the incident energy fluence.

In some implementations of the second aspect of the disclosure, to separate frequency components of the flood field signal, the controller is further configured to generate a fluence-signal-fitted model that models the frequency components characteristic of variations in the incident energy fluence.

In some implementations of the second aspect of the disclosure, the fluence-signal-fitted model has a frequency cut-off characteristic of topological properties of the incident energy fluence.

In some implementations of the second aspect of the disclosure, the frequency cut-off is a maximum in-field energy fluence gradient of the incident energy fluence.

In some implementations of the second aspect of the disclosure, the fluence-signal-fitted model is a surface-fit polynomial model, a surface fitting model, a regional-surface fitting model, a weighted-surface fitting model, a signal smoothing model, a low-pass filter model, a signal frequency decomposition model, a Fourier analysis model, or an image denoising model.

In some implementations of the second aspect of the disclosure, the fluence-signal-fitted model satisfies a condition that a derivative of an incident energy fluence integral with respect to the fluence-signal-fitted model is minimized.

In some implementations of the second aspect of the disclosure, the controller is further configured to correct the flood field signal for background dark-field and/or bad pixels to produce a corrected image signal.

In some implementations of the second aspect of the disclosure, to determine the pixel sensitivity matrix, the controller is further configured to adjust the corrected image signal by the fluence-signal-fitted model. For example, the corrected image signal may be divided by the fluence-signal-fitted model. In another example, the fluence-signal-fitted model may be subtracted from the corrected image signal. Other adjustments to the corrected image signal based on the fluence-signal-fitted model are contemplated.

In some implementations of the second aspect of the disclosure, the controller is further configured to capture an image with the image detector of an object irradiated by energy fluence produced by the signal source and correct the image of the object using the pixel sensitivity matrix.

In some implementations of the second aspect of the disclosure, the image detector is an electronic portal imaging device.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
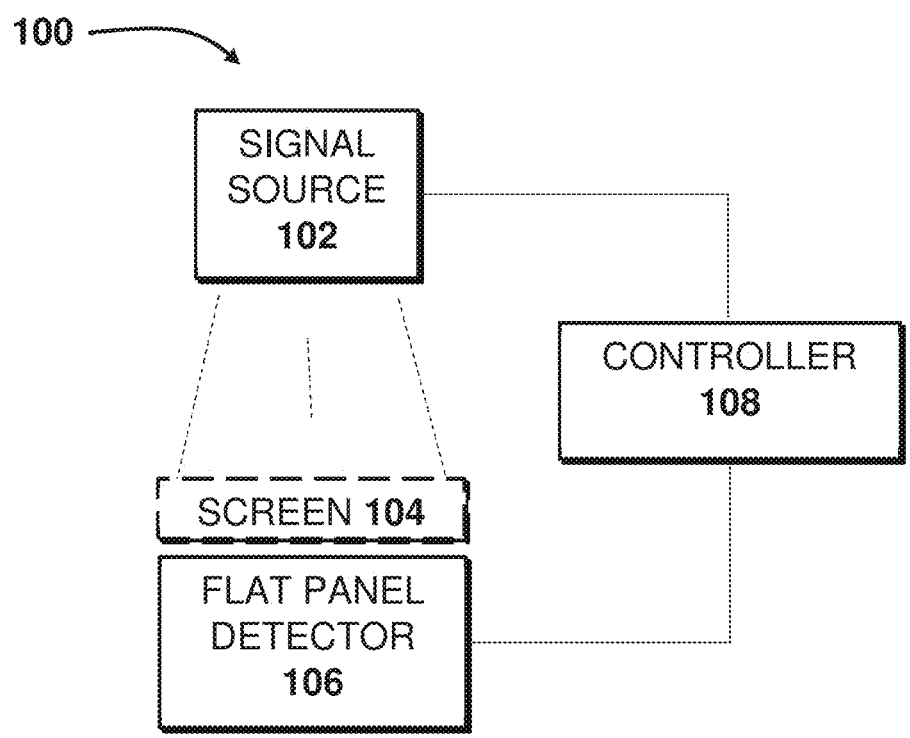
FIG. 1 is a system block diagram for an imaging system, suitable for implementing the several embodiments of the disclosure.

It should be understood at the outset that although illustrative implementations of one or more embodiments are illustrated below, the disclosed systems and methods may be implemented using any number of techniques, whether currently known or in existence. The disclosure should in no way be limited to the illustrative implementations, drawings, and techniques illustrated below, but may be modified within the scope of the appended claims along with their full scope of equivalents. Use of the phrase "and/or" indicates that any one or any combination of a list of options can be used. For example, "A, B, and/or C" means "A", or "B", or "C", or "A and B", or "A and C", or "B and C", or "A and B and C".

Disclosed herein is a new procedure to compute a pixel sensitivity map (PSM) for Electronic portal imaging device (EPID) detectors. The PSM is determined for EPIDs using a single flood field signal. The method includes obtaining the uncorrected signal from irradiation of the whole active EPID panel with an open radiation field. The method then determines the PSM by separating the high-frequency pixel-to-pixel sensitivity variations from the low-frequency radiation energy fluence variations and the periodic imaging panel features. The PSM is computed for multiple beam energies, with and without flattening filters. The method to compute the PSM does not require shifting the EPID panel, and therefore is not subject to error-propagation buildup inherent to panel-shifting methods. Furthermore, the shift-less method can be used as an automatic imager calibration procedure which is applicable to fixed-geometry imaging panels, such as those installed on Varian Ethos® and MR linac treatment machines.

The PSM is a map of the relative sensitivity of the individual imager pixels. It is used to convert the raw pixel signal measured by the imager, into the energy fluence-dependent detector signal (shorted to fluence-signal in the remainder of the document) through correcting for detector-element dependent sensitivity variations. Despite not knowing the exact fluence-signal, the incident energy fluence topological properties have a known frequency cut-off. The topological features of the imager and its read-out are also known. Therefore, the PSM is ascertained by obtaining a raw signal, removing background signal and imager-panel features, then separating high- and low frequency features. The low frequency features correspond to the incident radiation fluence-signal and the high frequency features corresponds to the detector-element dependent perturbations.

A raw EPID signal results from the incident particle energy fluence, the inherent pixels response, and the background signal. In large open fields, particle energy fluence is a slow varying signal that is locally considered spatially-constant. Pixel response is a fast and abrupt varying behavior. The background signal is due to the EPID panel electronics which is determined during radiation absence.

To determine the PSM, after correcting for the background signal, a model is applied that captures the underlying smooth particle energy fluence-induced-signal. This fluence-signal-fitted model is then used to determine the PSM. For example, the EPID flood image may be adjusted using the model (e.g., scaled by the model or having the model subtracted from the EPID flood image) to determine the PSM.

An EPID image results from the incident energy fluence interacting with the EPID detection unit, resulting in the creation of secondary electrons which interact with a screen and/or the pixel photo-diodes. For the EPIDs in various examples provided herein, the majority (~90%) of the radiation induced signal recorded by pixel photo-diodes, $I_{raw}(x, y)$ is from light produced from electron and photon interactions with a $Gd_2O_2S{:}Tb$ screen, while the remaining signal is from direct interactions with the photo-diodes. The raw measured EPID signal is due to three main components, namely: the incident particle energy fluence, the inherent imager response to the incident energy fluence, and the detector background signal. Thus, the raw pixel reading at position (x, y) on the EPID coordinate system is formulated as $$I_{raw}(x,y)=\Psi(x,y)\otimes P(x,y)+I_{bg}(x,y), \quad (1)$$

where $I_{raw}(x, y)$ is the raw pixel signal, $\Psi(x, y)$ is the energy fluence incident on imager at the pixel location, P (x, y) is the EPID pixel detector-element response, and $I_{bg}(x, y)$ is the pixel background (e.g., a signal recorded when there is no incident fluence).

The pixel sensitivity matrix, P (x, y)∀(x, y), accounts for the relative spatially differential response of the screen plus the photo-diode and its read-out, whether it is from the spatially non-uniform response of the screen, differential energy dependence of the screen response, non-uniform response of the photo-diode signal generation and detection, or the photo-diode read-out electronics. While P (x, y) could be sub-divided into a product of factors for each of the above-mentioned sub-components, such sub-division provides no benefit in determining and correcting for the PSM. The raw pixel signal after subtracting the background hereafter is called the corrected pixel signal:

$$I_c(x,y)=I_{raw}(x,y)-I_{bg}(x,y), \quad (2)$$

where $I_c(x, y)$ is the corrected pixel signal, $I_{raw}(x, y)$ is the raw pixel signal, and $I_{bg}(x, y)$ is pixel background.

The PSM method is based upon the fact that the signal $I_c$ results from a smooth energy fluence surface $\Psi$ superimposed with the spatially-dependent detector response P. P can therefore be estimated and/or modeled by removing frequency components greater than a maximum energy fluence gradient via multiple different methods. For example, P can be modeled using Fourier analysis, image denoising, or surface fitting. In various implementations, during the modeling of P, the EPID's pixel defect map may be used to exclude the contribution of bad or unresponsive pixels to the fitted model. Equation (1) treats EPID pixels in a spatially-independent manner; therefore, a pixel whose signal is not proportional to the incident energy fluence does not impact its adjacent pixel readings, but rather may be treated as a bad pixel where its value could be computed from the mean or median of its neighbor pixel values.

For therapy linacs, in flattening-filter-free (FFF) mode, the energy fluence shape is characteristic of Bremsstrahlung radiation sources, a center-peaked smooth energy fluence surface which broadens as it moves away from the radiation source. When a flattening filter is utilized, the in-air energy fluence is nominally flat, but the in-air energy fluence surface attains a dip at the beam central axis and has off-axis horns. For both FFF and flattened beams the energy fluence profile is smooth with low gradients. In the absence of beam collimating and added attenuating devices, the maximum in-field energy fluence gradient measured in air occurs for highest energy FFF beams at close proximity to the radiation source. In an example, a 10X FFF beam measured at SID equal to 100 cm has a maximum gradient of 0.41%/mm, while for a 6X FFF beam the maximum gradient is 0.28%/mm measured at the same SID.

In an example, for simplicity, a polynomial is fit to $I_c$ that describes the underlying smooth energy fluence surface, but is incapable of capturing the high frequency pixels sensitivity changes. The polynomial-based regression surface model in both x and y dimensions is used to model the fluence-signal-fitted model. Since most of the fluence-signal is represented by the area under slow-varying envelopes, an optimal fitting model is defined herein as the minimal-degree model which captures most of the measured fluence. Mathematically, an optimal fitting model satisfies the condition that the derivative of the fluence-signal integral with respect to the model degree is ideally zero.

Equation (1) has two spatially-dependent unknown terms $\Psi(x, y)$ and P (x, y). The open field $\Psi(x, y)$ used in the pixel calibration has low spatial variations, which when combined with the sharpness of EPID energy deposition kernels allows the convolution in Equation 1 to be simplified to a multiplication with sufficient accuracy for the purposes here.

Extracting the PSM can be accomplished using:

$$P=I_C/\Psi \text{ if } \Psi=\Psi(x,y)\forall(x,y), \quad (3)$$

where P is the spatially-dependent detector response, $I_C$ is the corrected pixel signal, and $\Psi$ is the energy fluence incident on imager at a pixel location. As described above, the corrected pixel values $I_C=I_c(x, y)\forall(x, y)$ are known. Since $I_C$ and $\Psi$ are not independently known, we decouple $\Psi$ and P by utilizing their fundamental characteristics to determine $I_c$; $\Psi$ has spatial variation characteristics of the incident fluence, while P has characteristics of relative pixel response.

To validate the generated PSM, PSMs are computed for multiple beam energies are measured with and without flattening filters and for multiple source-to-imager distances. Since the PSM is a detector characteristic, it should be independent of the beam energy and source-to-imager distance (SID) variables. Inter-comparative measurements of fixed slit fields with the EPID being shifted between measurements is also performed.

In an experiment, the fluence-signal of the flattening-filter-free (FFF) beams were optimally modeled as a 12th degree polynomial surfaces which had ≤0.1% residuals near the central axis. A 6 MV FFF PSM and a 10 MV FFF PSM were within ~0.1%, and independent of the EPID SID, suggesting that the PSM is energy independent. PSMs from a 6 MV, 10 MV, and 15 MV flattened-beam were well-modeled as 12th degree polynomial surfaces, which were equivalent within ~0.24% but differed from the FFF PSM by up to 0.5% near the beam central axis. Applying the FFF PSMs to the flattened-beam measurements reduced the central-axis deviation between the raw and corrected signal to <0.1%, confirming the PSM energy independence hypothesis. When the FFF PSM is utilized, output verification with shifted slit deliveries agreed within ~0.5% for all beam energies, which is within the radiation delivery uncertainty of ~0.57%.

PSM for MV EPIDs can be determined by separating out the slowly varying, well behaved fluence-signal from the pixel-to-pixel sensitivity variations. The quality of the PSM is found to be dependent on the quality of the surface fit, which is best for the 6 MV FFF beam measured at an SID equal to 180 cm. Within fitting errors, the PSM is independent of beam energy for 6, 10, and 15 MV beams with and without flattening filters. The PSM generation does not require shifting the EPID panel nor multiple EPID panel irradiations and should be usable for linacs with fixed geometry EPIDs.

FIG. 1 is a system block diagram for an imaging system 100, suitable for implementing the several embodiments of the disclosure. The imaging system 100 includes a signal source 102, a flat panel detector 106, and a controller 108.

The signal source 102 directly or indirectly provides incident energy fluence for detection by the flat panel detector 106. For example, the signal source 102 may be a linear accelerator that irradiates a phosphorescing screen 104, such as a $Gd_2O_2S$:Tb screen for generating an indirect incident energy fluence on the detector 106. In other examples, the signal source 102 may be a light source for generating and directly supplying an incident energy fluence on the detector 106. In another example, a laser may directly or indirectly supply an incident energy fluence on the detector 106. For example, upon irradiation of tissue at a particular frequency, the laser may induce fluorescence in the tissue so as to supply an incident energy fluence on the detector 106. Other examples of the signal source 102 directly or indirectly supplying an incident energy fluence to the detector 106 are contemplated by this disclosure.

The flat panel detector 106 may be any detector suitable for detecting an incident energy fluence supplied by the signal source 102. In various examples, the detector 106 may be a two-dimensional array, a linear array, or any other known configuration of energy fluence detectors (e.g., imaging sensors). The detector 106 may be mounted in a stationary position, moveable in a coupled relationship to the signal source 102 (e.g., as the detector 106 is moved, the signal source 102 is likewise moved to maintain an initial relative spatial configuration between the detector 106 and the signal source 102), moveable in a manner independent from the signal source 102, or any other known spatial configuration of a detector 106. In various implementations, one or more filters, lenses, or other optical elements (not shown) may be positioned within a path between the signal source 102 and the detector 106.

The controller 108 is electrically coupled to the signal source 102 and the detector 106. The controller 108 is configured to control operation of the signal source 102. For example, the controller 108 is configured to initiate generation of an imaging signal for causing an energy fluence signal to be incident on the detector 106. For example, the controller 108 may control the timing of when to initiate signal generation, a power level, frequency, duration, modulation, or any other characteristic of the generated imaging signal.

The controller 108 is also configured to capture and process images read from the detector 106. For example, the controller 108 is configured to capture a dark field image, a flood field image, and a raw image. The controller 108 uses the dark field image to capture the flood field image to produce a corrected image signal, described above. Likewise, the controller 108 is configured to generate or receive a model of the incident energy fluence of the flood field image. For example, the model may be generated on a separate device (not shown) and supplied to the controller 108. The controller 108 is configured to generate a PSM for the detector 106 using the corrected image signal and the model, as described above. The PSM may be stored locally on a memory accessible to the controller 108 or on a remote calibration server (not shown). Upon capturing the raw image, the controller 108 is configured to correct the raw image using the PSM. Alternatively, the controller 108 supplies the captured images to an external device (not shown) for performing the processing described above.

In various implementations, the controller 108 may periodically generate a new PSM. For example, after a predetermined period of time (e.g., hours, days, years), a predetermined number of imaging cycles (e.g., 10, 100, 1000, 10,000), or other periodic occurrence, the controller 108 may generate a new PSM to replace a prior PSM for the detector 106. In some implementations, because there is no need to shift the detector panel 106, the controller 108 may generate a new PSM at each imaging operation.

While one controller 108 is shown, it is contemplated that separate controllers may be provided for controlling the signal source 102, capturing image signals read from the detector 106, and processing the captured image signals. Other variations of the control architecture of the system 100 are contemplated by this disclosure.

Figure 2:
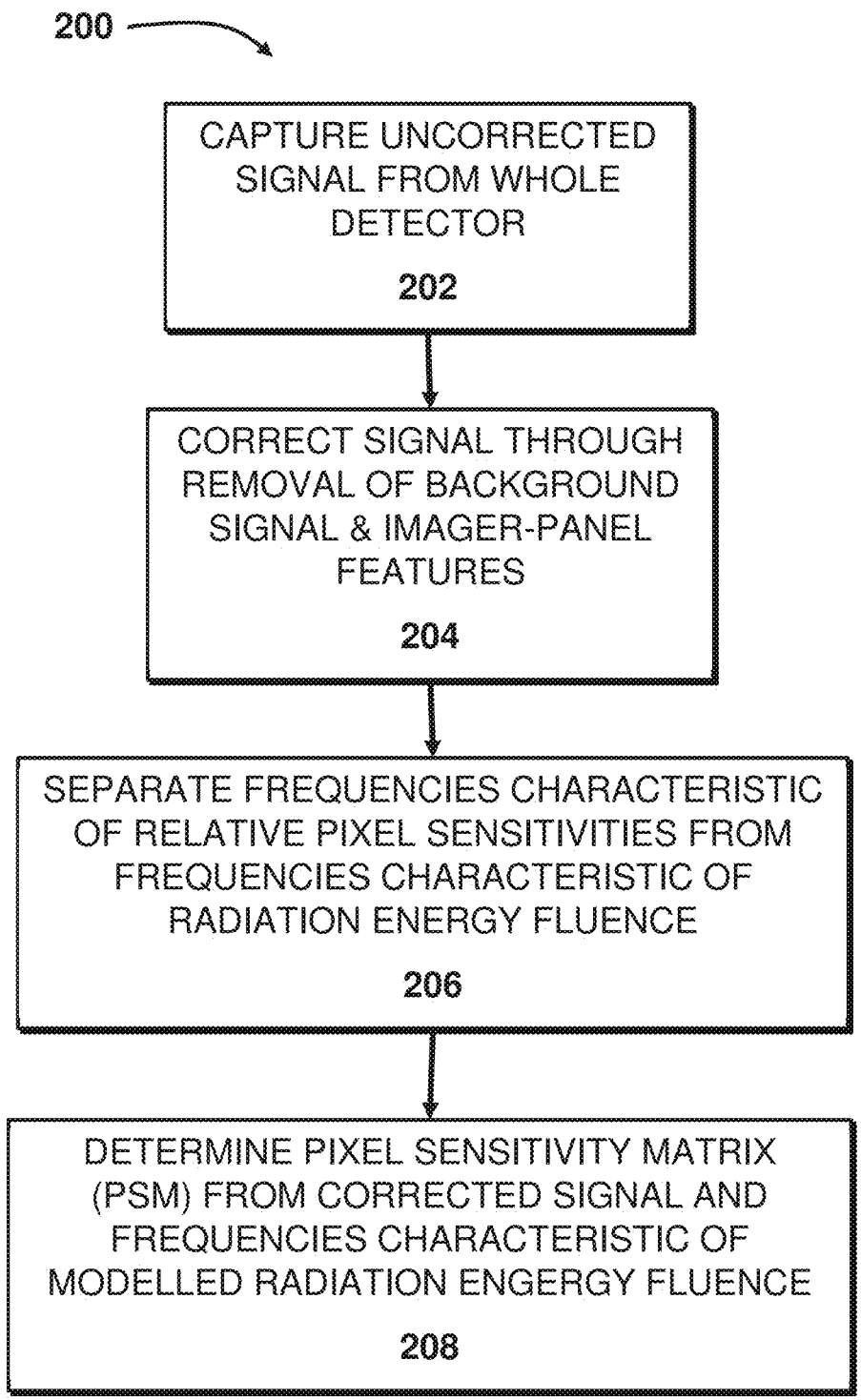
FIG. 2 is a calibration method for the imaging system of FIG. 1, suitable for implementing the several embodiments of the disclosure.

FIG. 2 is a calibration method 200 for the imaging system 100 of FIG. 1, suitable for implementing the several embodiments of the disclosure. At 202, the signal source 102 generates an imaging signal for producing an incident energy fluence on the detector 106. The controller 108 captures a flood field image generated by the incident energy fluence on the detector 106. At 204, the controller 108 generates a corrected image through correction of the flood field image by removal of a background signal and effects of known image-panel features. For example, a dark field image may be captured by the controller 108 and subtracted from the flood field image to remove the background signal. Additionally, the controller 108 may use a dead/bad pixel map of the detector 106 and replace the values of dead/bad pixels with an average value of their surrounding neighboring pixels. Other known corrections for dead/bad pixels are contemplated by this disclosure.

At 206, the controller 108 processes the corrected image to separate frequencies characteristic of relative pixel sensitivities from frequencies characteristic of radiation energy fluence. For example, the incident energy fluence has a known maximum in-field energy fluence gradient. The controller 108 generates or receives a model that describes the incident energy fluence on the detector 106. The corrected image is modeled at frequencies at or below the maximum in-field energy fluence gradient. For example, the model may be a polynomial fit of the surface of the incident energy fluence on the detector 106 up to the maximum in-field energy fluence gradient, a Fourier transform of the corrected image truncated at the maximum in-field energy fluence gradient, or any other image denoising technique to separate frequencies in the corrected image above the maximum in-field energy fluence gradient.

At 208, the controller 108 generates the PSM from the corrected image and the frequencies characteristic of radiation energy fluence. That is, the controller 108 generates the PSM by adjusting the corrected image with the model of the incident energy fluence on the detector 106. For example, the controller 108 may divide the corrected image signal by the model or subtract the model from the corrected image. Other mathematical operations for adjusting the corrected image with the model to generate the PSM are contemplated by this disclosure.

Figure 3:
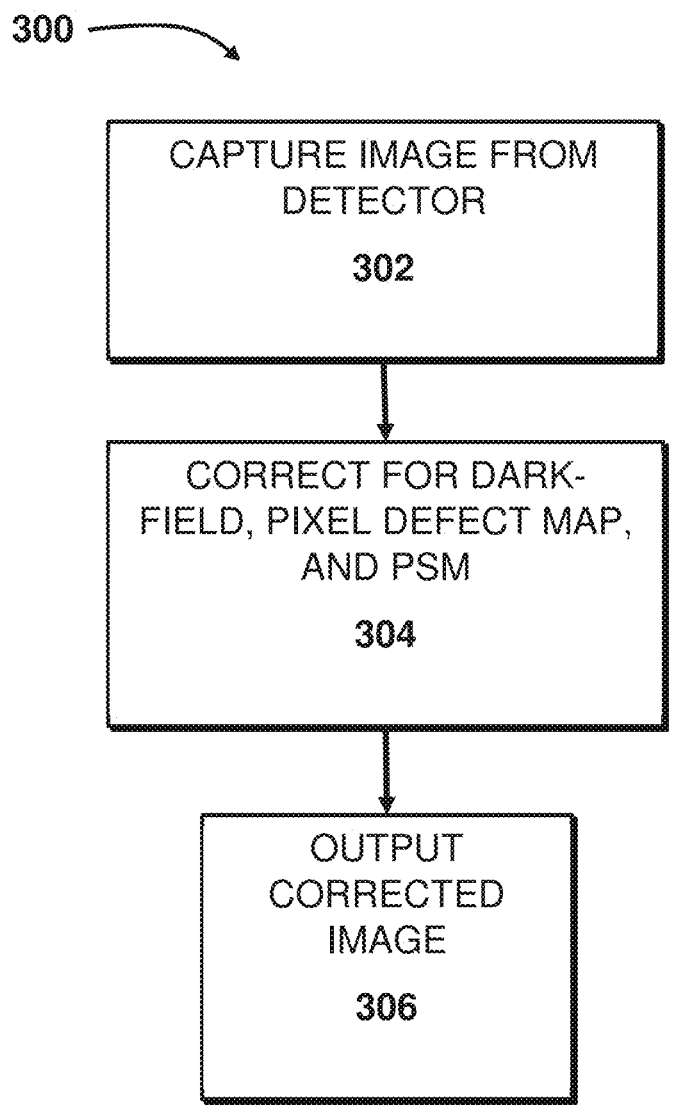
FIG. 3 is an image capture and correction method for the imaging system of FIG. 1, suitable for implementing the several embodiments of the disclosure.

FIG. 3 is an image capture and correction method 300 for the imaging system 100 of FIG. 1, suitable for implementing the several embodiments of the disclosure. After obtaining the PSM of the detector 106, raw images captured by the detector 106 may be corrected using the PSM. At 302, the controller 108 captures a raw image from the detector 106. At 304, the raw image is corrected for background signal (e.g., dark field image is subtracted from the raw image), a dead/bad pixels (e.g., map of the dead/bad pixels for the detector 106 is used to replace the values of dead/bad pixels with an average value of their surrounding neighboring pixels), and PSM (e.g., the PSM is subtracted from the raw image). Other image correction methods and mathematical operations for correcting the raw image using a dark-field image, dead/bad pixel map, and PSM are contemplated by this disclosure. At 306, a corrected image is generated and output by the controller 108. For example, the corrected image may be stored locally or transmitted to an external device for storage, viewing, or further processing.

Example 1

In various examples, measurements were performed with an amorphous silicon EPID aS1000 mounted on TrueBeam linear accelerator (Varian Medical systems, Palo Alto, CA, USA). The aS1000 spatial resolution is 1024×768 pixels covering an active detector area of 40×30 cm$^2$. The dimensions of a single detector pixel are 0.039×0.039 cm$^2$. The aS1000 EPID has a maximum off-axis shifts equal to 15, 16, 6, and 7 cm in the +x, −x, +y, and −y directions, in the linear accelerator coordinate system, respectively. In the z-axis, the maximum and minimum SIDs are 183 and 95 cm, respectively. EPID measurements were acquired at SIDs equal to 100, 150 and 180 cm for 6, 10, and 15 MV beams with flattening filters (WFF) in addition to 6 and 10 MV flattening filter free (FFF) beams.

Data Acquisition and Calibration

A QA system is used for image acquisitions and utilization of the generated PSM. This avoids the need to reconstruct the raw EPID images from the background and flood-field corrected images available from the Varian X-Ray Imaging System (XI).

The QA system utilizes an independent frame grabber on an independent computer to directly read the cine raw images in real-time as they are acquired at ~10 Hz. The Varian EPID software was set to acquire images in dosimetry mode, which, for the TrueBeam 1.5 system used, may be configured to yield images with no correction/calibration for the dark-field, flood field, or beam profile by the treatment console software. Corrected EPID signals acquired in either imaging or dosimetry mode would work with the method, as would images acquired directly with the XI system, provided that the raw images were reconstructed from the corrected EPID images. Per-frame EPID signal saturation was avoided by using the lowest possible dose rates for the FFF beams, i.e., 600 MU/min for 6X FFF and 400 MU/min for 10X FFF. For each source-to-imager distance (i.e., 100 cm, 150 cm and 180 cm), the open-field size was set to cover the active area of the imaging panel, i.e., 40×30 cm$^2$ at the SID plus an extra 0.5-1.0 cm margin beyond the imager boundary.

Each EPID image processed resulted from a cine acquisition of image frames until a total of 250 MUs are delivered. The large MU deliveries were used to minimize the effect of readout artifacts. Post-acquisition, partial image frames acquired at the beginning and end of the beam delivery were removed, and the remaining frames are summed. Ignoring the partial frame removal would have had a<<1% effect on the PSMs for 250 and greater MU deliveries.

The pixel defect map (PDM) for the EPID device is obtained from the linac calibration data repository. The PDM is computed during the periodic EPID calibration process by the linac manufacturer algorithms. The map is used to identify the dead/bad pixels on the imager panel and replace their values with the average value of their surrounding neighboring pixels.

Imager background used in the processing was from a (temporally local) background collection; the average of 250 frames recorded during a beam-off session was sufficiently delayed from the beam-on session to guarantee a ghosting-free EPID signal, but within the measurement session. Signal collection is integrated into a single image for two main reasons; first, the apparent banding artifact of individual images tend to wash out in the averaging process. Second, the integration improved the total signal-to-noise ratio, thereby reducing uncertainty in the associated computed pixel sensitivity map. For the aS1000, the amorphous-silicon pixel array consists of 128 pixel columns connected to independent channel charge amplifiers. A gate driver is connected to the rows of a pixel array which stages the image readout through the pixels thin film transistors (TFT). Thus, the aS1000 EPID has 8 vertical signal reading groups which may feature step-wise linear-signal patterns due to independent circuitry. After dark current and defective pixel correction of the EPID image, the linear signal trends, in the 128×768 sub-panels for aS1000 EPID, are corrected through the following signal "de-banding" method.

First, the signal of each reading group is separated into linear and non-linear terms. The linear term is the best-fit plane (i.e., 128×768 pixels for a sub panel of an aS1000 EPID) calculated through the least-square method. The non-linear term is the signal fluctuating around the best-fit plane. Second, the y-coefficient (i.e., the slope) of the best-fit plane equation is set to zero so that signal gradient in the y direction is eliminated. This procedure corrects for any distortion of the measured signal due to beam asymmetry in the y direction or the multiplexed signal readout of the pixel matrix rows of diodes. Lastly, continuity of the signal is enforced for all best-fit planes, of all sub panels, at the boundaries in the x-direction. This step involves equating the offset term of plane equation calculated for all sub panels of the EPID active matrix. This procedure normalizes the linear/step-wise features of the full EPID signal.

Regression Approach Validation

Since the PSM is characteristic of the detector and its associated readout, it should be independent of the beam delivery mode, the EPID source-to-imager distance (SID), and lateral offsets of the EPID. As such, PSMs are independently determined for each photon beam delivery mode available on the linac at multiple SIDs, then these PSMs are intercompared to establish independence. In total, PSMs were computed for 15 different beam configurations, resulting in 15 different fluence polynomial models for the measured signals at 3 different SIDs (i.e., 100 cm, 150 cm, and 180 cm), 3 different energies (i.e., 6MV, 10MV, and 15MV) and 2 different flattening filter configurations (WFF and FFF for 6MV and 10MV). The pixel-by-pixel deviations of these PSMs is evaluated to quantify the PSM precision. In this process, the preferred delivery mode and SID for determining the PSM was also identified. For fixed radiation fields, field measurements were inter-compared spanning a range of lateral offsets that could be attained by the imager to confirm position independence. This, in effect, cross-validates the method with those who inter-related shifted EPID measurements to derive the PSM. For this series of measurements, the imager was placed at the isocenter plane and the jaws adjusted to produce long-narrow beams (slits) on the EPID imager. In the imager x-direction, a 2 cm (~50 pixels) by 30 cm x-slit is formed. Image resulting from repeated 250 MU deliveries were acquired, with the EPID shifted between acquisitions by distances equal to 2n cm, where n=±1, ±2, ±3, . . . , until the full EPID extent is covered. Similarly, acquisitions with a 40 cm by 1 cm y-slit were acquired. The consistency of the presently disclosed PSM with the PSM one would get with a shifting method is evaluated by evaluating the pixel-wise variance in the x-slit and y-slit output measurements.

Results

Input Signals and Fluence-Signal Fits

Figure 4A:
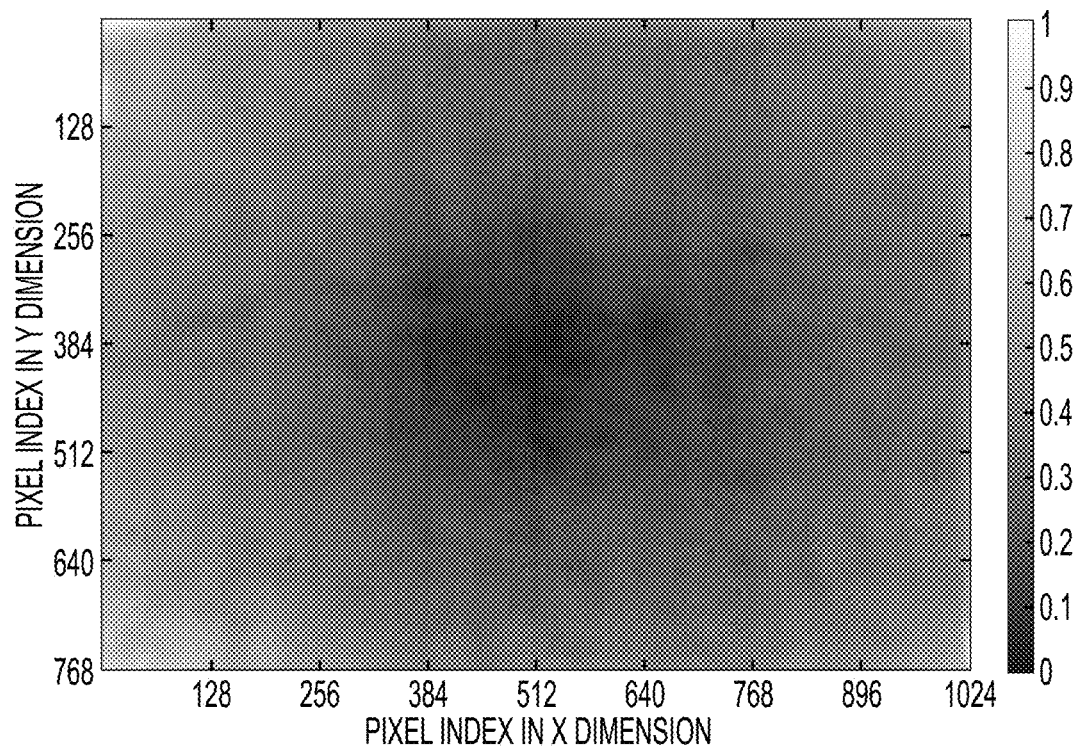
FIG. 4A is an example of a corrected electronic portal imaging device (EPID) signal for a 6 MV beam with a flattening filter acquired at source-to-imager distance (SID) equal to 150 cm, suitable for implementing the several embodiments of the disclosure.
Figure 4B:
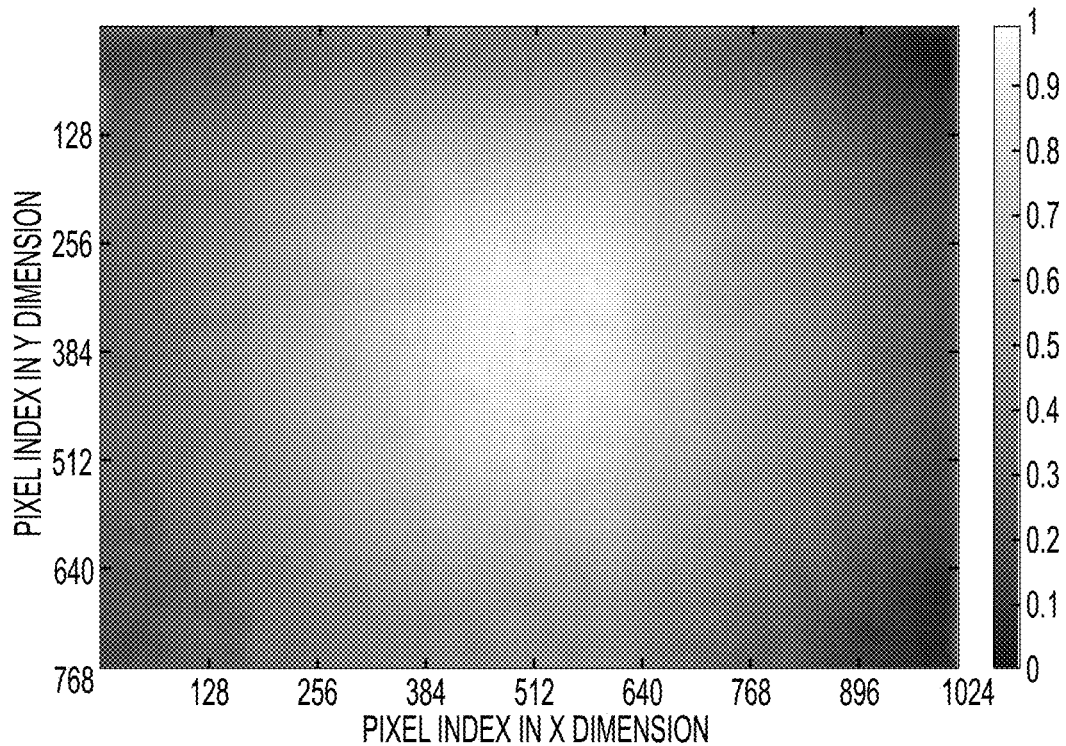
FIG. 4B is an example of a corrected EPID signal for a 6 MV flattening-filter-free (FFF) beam acquired at a SID equal to 180 cm.

Two 6 MV flood field EPID images for the aS1000 EPID panel, that were used as inputs to the PSM generation algorithm, are shown in FIGS. 4A and 4B. FIG. 4A is an example of a corrected EPID signal for a 6 MV beam with a flattening filter acquired at SID equal to 150 cm. The signal in FIG. 4A has the beam flattening filter and was acquired at SID equal to 150 cm. FIG. 4B is an example of a corrected EPID signal for a 6 MV FFF beam acquired at a SID equal to 180 cm. The image in FIG. 4B is for FFF beam and was acquired at SID equal to 180 cm. Both signals were corrected for background dark-field and bad pixels, then normalized to the range [0,1]. Faint vertical strips can be seen in the images, particularly at n×128 pixel indices, where n=1 to 7 in the x-direction, due to differences in the electronic readout of the detector sub-panels despite the fact that EPID step-wise, i.e., sub-panel, signal features were normalized using the signal "de-banding" method discussed above. These residual bands are inconsequential.

Figure 4C:
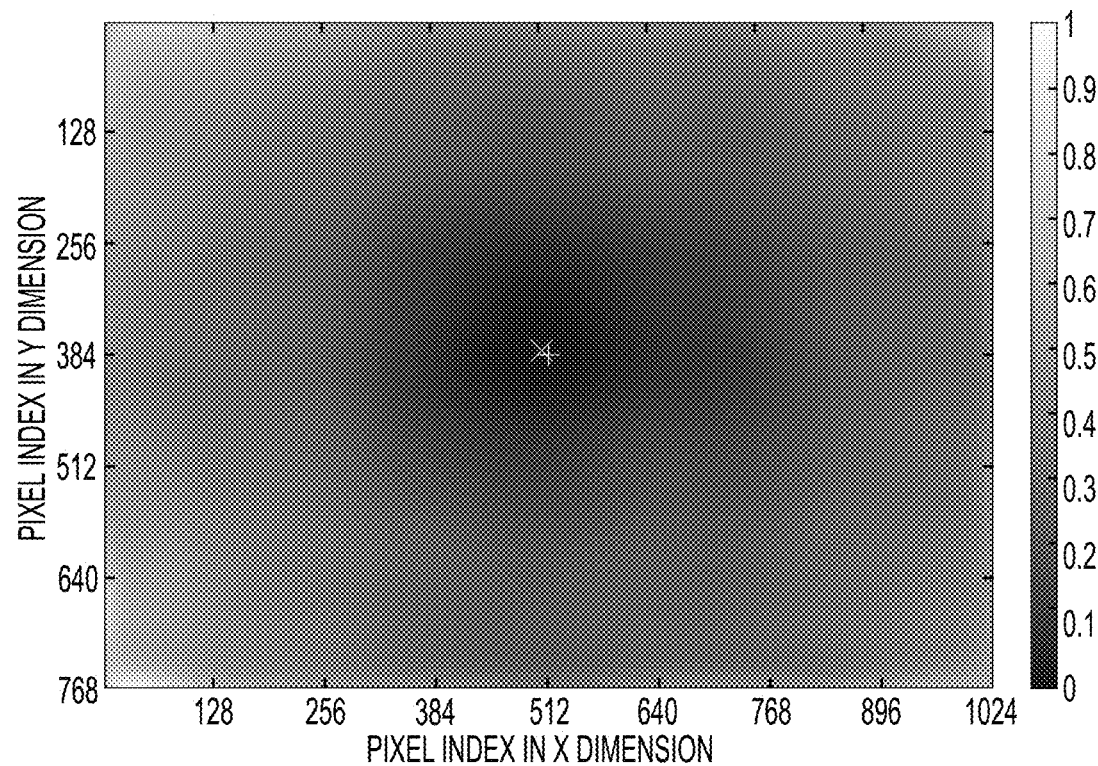
FIG. 4C is a surface fitted to the signal in FIG. 4A, suitable for implementing the several embodiments of the disclosure.
Figure 4D:
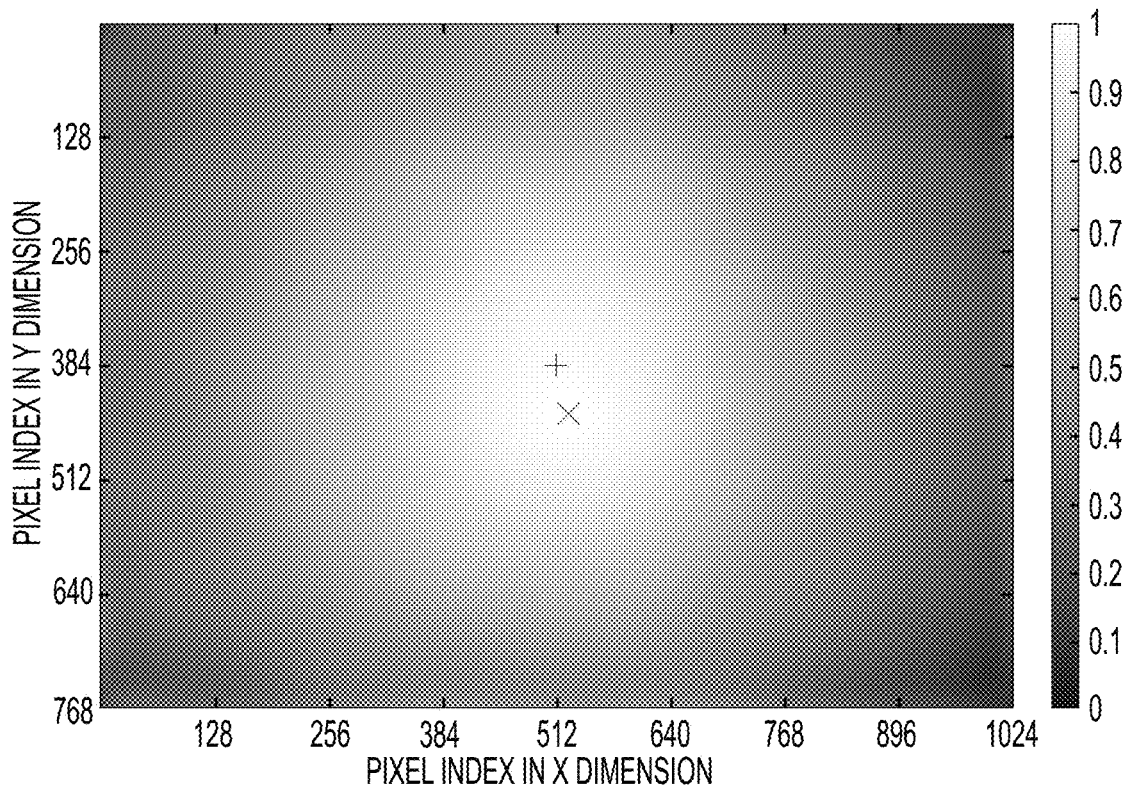
FIG. 4D is a surface fitted to the signal in FIG. 4B, suitable for implementing the several embodiments of the disclosure.

FIGS. 4C and 4D show the fitted fluence-signal surfaces to the flattened beam signal of FIG. 4A and the FFF beam signal of FIG. 4B, respectively, after the application of the sub-panel corrections. That is, FIG. 4C is a surface fitted to the signal in FIG. 4A and FIG. 4D is a surface fitted to the signal in FIG. 4B. The EPID central pixel is marked with a '+' and the fluence-signal maximum or minimum is marked with a 'X' in FIGS. 4C and 4D. The virtual fluence-signal surfaces shown in FIGS. 4C and 4D are constructed using a polynomial model of the form:

$$\Psi(x, y) = \sum_{n=0}^{Ox} \sum_{m=0}^{Oy} p_{nm} x^n y^m, \quad (4)$$

where the coefficients $p_{nm}$ are found via linear least squares regression. The fits shown are for a 12-degree polynomial fits in the x and y directions.

FIGS. 4C and 4D also show locations of the beam's central axes ('+' symbol) and the minimum and maximum of the fitted fluences ("x" symbol) of FIGS. 4A and 4B, respectively. The offset is primarily in the y-direction. In the x-direction, FIGS. 4C and 4D show the fitted surface symmetry which is impacted only by the actual beam symmetry in the x-direction. Moreover, the curvatures of the fitted surfaces are different because of the existence of the flattening filter in the beam of FIG. 4C which shows the slowly rising off-axis horns compared to the fast declining of the forward-directed FFF beam of FIG. 4B. The fitted surfaces can be clearly identified as concave and convex, from the beams eye-view direction, for flattened 6 MV beam in FIG. 4C and the FFF 6 MV beam in FIG. 4D, respectively.

Figure 4E:
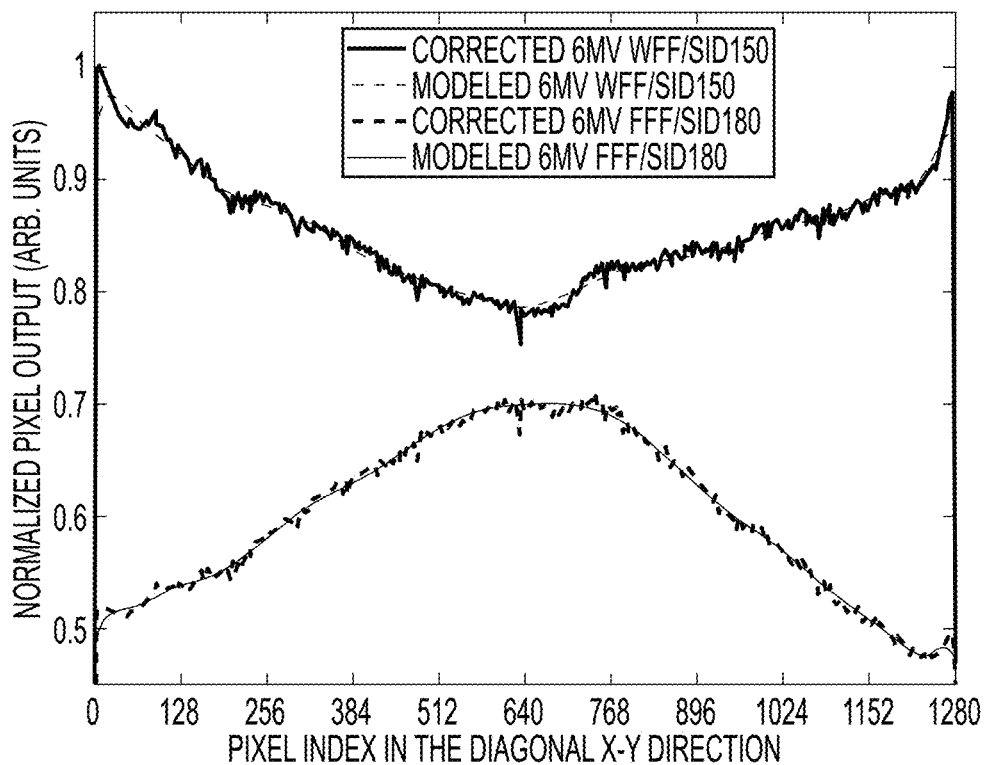
FIG. 4E are diagonal profiles of signals that demonstrate how well the surface models of FIGS. 4C & 4D fit the corrected EPID images in FIGS. 4A & 4B.

FIG. 4E shows diagonal profiles of signals that demonstrate how well the surface models of FIGS. 4C & 4D fit the corrected EPID images in FIGS. 4A & 4B. FIG. 4E shows diagonal profiles of the corrected fluence-signals in FIGS. 4A and 4B overlaid with their corresponding surface model values from FIGS. 4C and 4D, respectively.

Figure 4F:
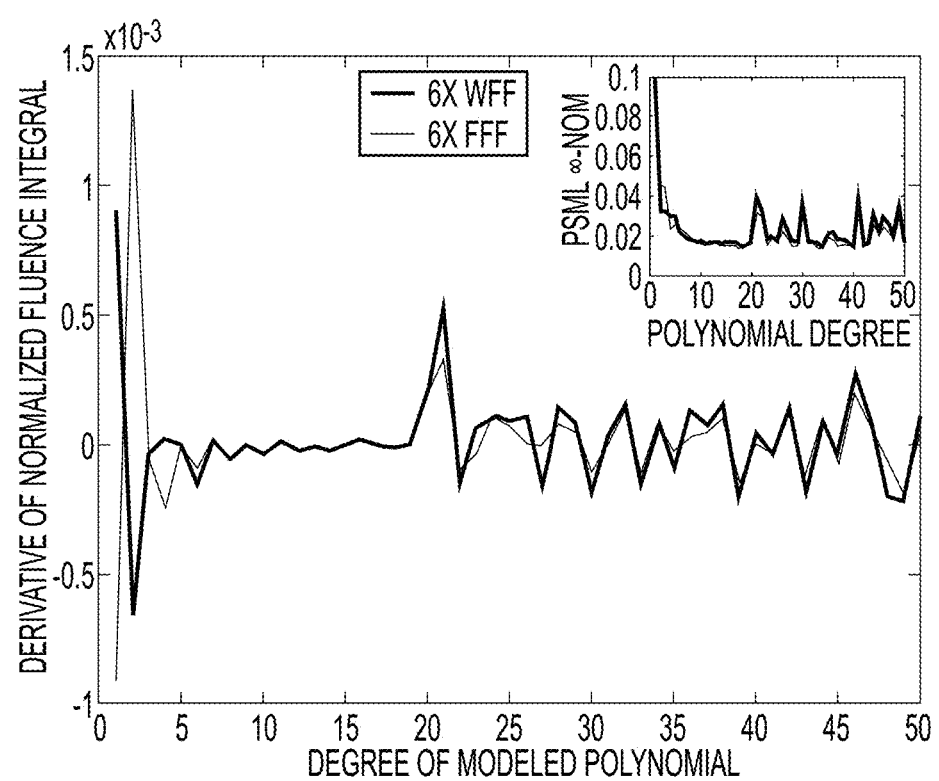
FIG. 4F is a convergence of fluence-signal derivative and the PSM L-norm during the extraction of the underlying fluence-signal in FIGS. 4A and 4B with various degrees of the polynomial-based fittings.

To determine the optimal order of the regression models in FIGS. 4C and 4D, a convergence test was conducted. The test involves successive calculation of the derivative of the fluence-signal integral using increasing cut-off polynomial order. Here a suitable cut-off limit was sought that maintains a fixed total measured fluence. The results of the convergence test are shown in FIG. 4F. FIG. 4F is a convergence of fluence-signal derivative and the PSM L∞-norm during the extraction of the underlying fluence-signal in FIGS. 4A and 4B with various degrees of the polynomial-based fittings. It was found that the derivative of the integral fluence-signal converges toward the $12^{th}$ order polynomial models, in the x and y dimensions, for both PSM models. The inset plot of FIG. 4F shows the maximum absolute output change for a 1×1 cm$^2$ radiation field (i.e., average of 25×25 pixels) by the PSMs under study. The infinity norms of the PSMs also converge approximately at the $12^{th}$ degree regression models. Due to complexities of the surface features introduced by the flattening filters, slightly better convergence is observed for the FFF beams PSM over the flattened beams PSM. In the inset plot of FIG. 4F, the minimum L∞-norm value represents the true variance in the PSM and the deviation from this value is an uncertainty in the measurement.

Thus, considering a delivery accuracy of ~0.5%, upon the application of this PSM to an EPID dose map, a relative dose accuracy within ≤2% is reached at a polynomial cut-off around $4^{th}$ degree for the FFF PSM and $5^{th}$ for the flattened beam PSM and a dose accuracy within ≤0.5% is achievable at a cut-off order of $10^{th}$ degree for the FFF PSM and $14^{th}$ degree for the flattened beam PSM.

Pixels Sensitivity Maps

Figure 5A:
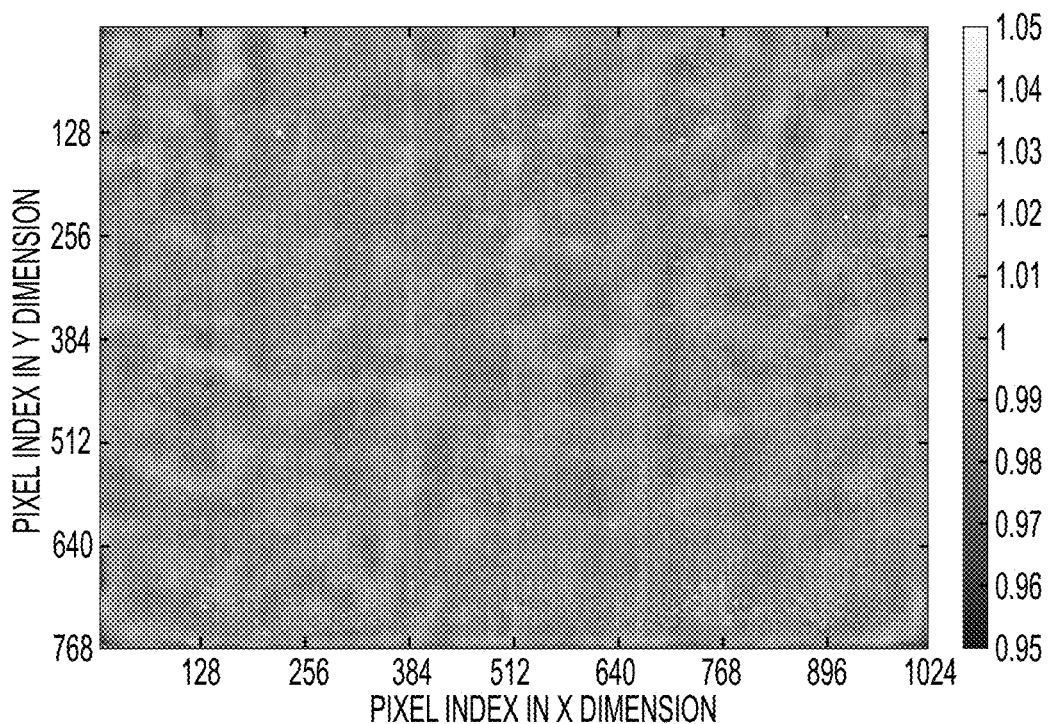
FIG. 5A shows a pixel sensitivity map (PSM) generated for a 6 MV flattened photon beam measured at SID equal to 150 cm.
Figure 5B:
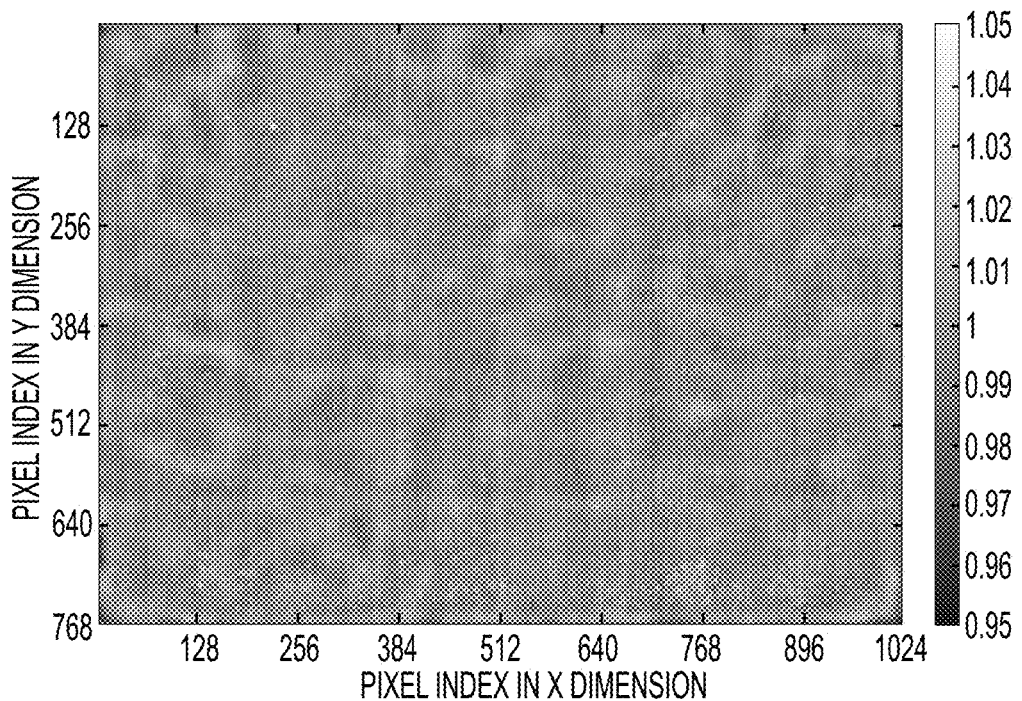
FIG. 5B is a PSM generated for 6 MV photon beam without flattening filter measured at SID equal to 180 cm.
Figure 5C:
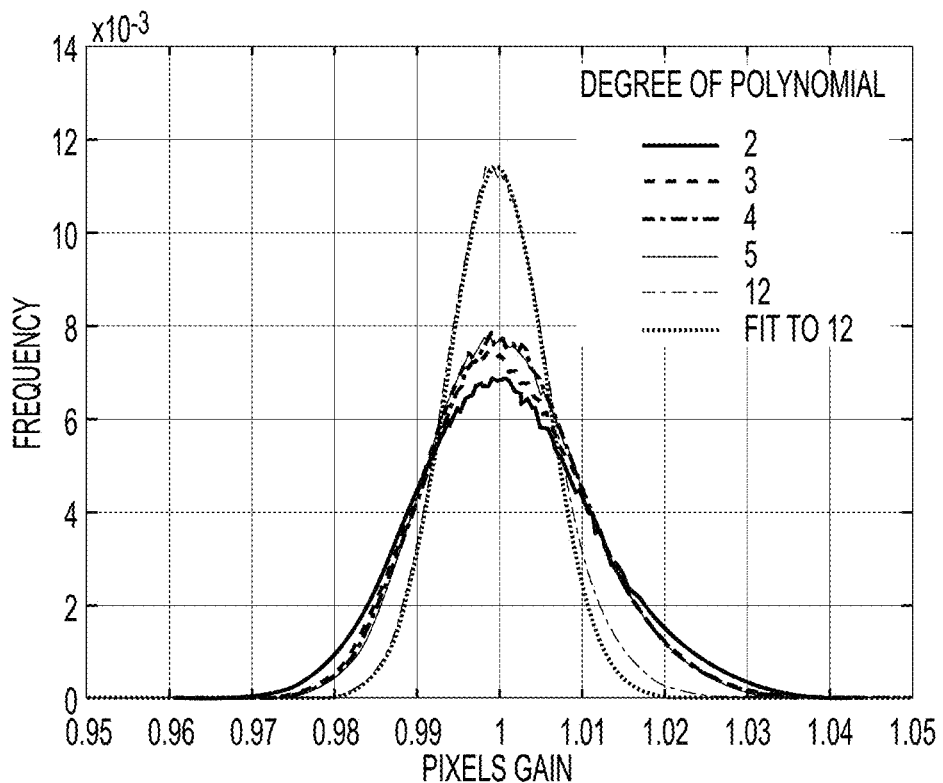
FIG. 5C is a graph showing the effect of changing the fitting model on a pixel sensitivity histogram for 6 MV beam with a flattening filter.
Figure 5D:
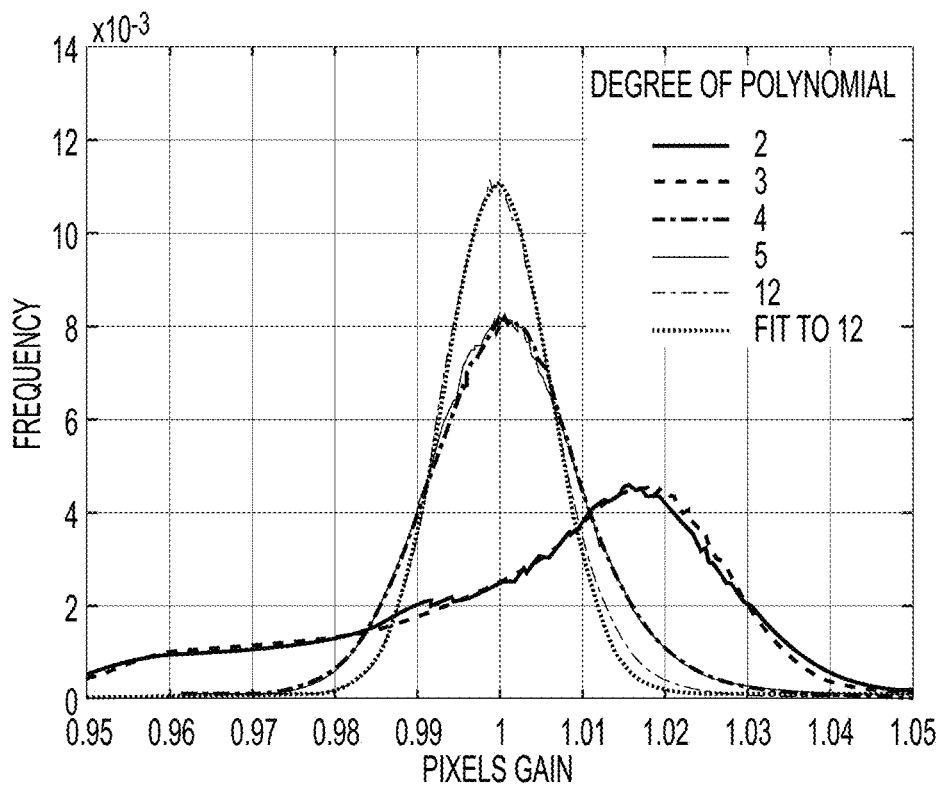
FIG. 5D is a graph showing the effect of changing the fitting model on pixels sensitivity histogram for 6 MV FFF beam.
Figure 5E:
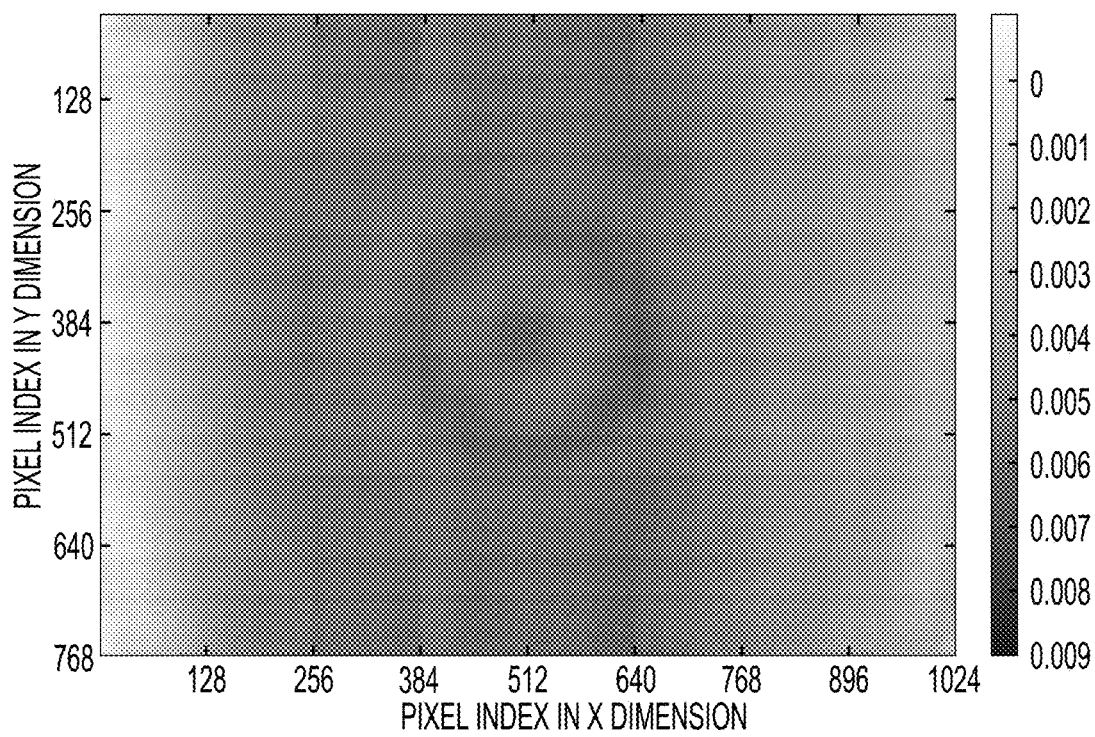
FIG. 5E shows a fractional error between signals in FIG. 5A & 5B.

The 12-degree polynomial fit generated pixel sensitivity maps for the beam configurations in FIGS. 4A and 4B are shown in FIGS. 5A and 5B, respectively. FIG. 5A shows a pixel sensitivity map (PSM) generated for a 6 MV flattened photon beam measured at SID equal to 150 cm. FIG. 5B is a PSM generated for 6 MV photon beam without flattening filter measured at SID equal to 180 cm. The mottling features of the two maps are similar, however, intensity differences near the PSM centers are apparent in the difference image of FIG. 5E. FIG. 5E is shows a fractional error between signals in FIG. 5A & 5B. Pixel sensitivity distributions of FIGS. 5A and 5B and for other order polynomial fits are presented in FIGS. 5C and 5D. FIG. 5C is a graph showing the effect of changing the fitting model on a pixel sensitivity histogram for 6 MV beam with a flattening filter. FIG. 5D is a graph showing the effect of changing the fitting model on pixels sensitivity histogram for 6 MV FFF beam. The legends indicate the order of the fitted polynomials in both x and y directions. The dotted black curves in FIGS. 5C and 5D are normal distributions fitted to the pixels sensitivity distributions with means equal to 0.9995 and standard deviations equal to 0.0055 and 0.0061 for PSM in FIGS. 5A and 5B, respectively.

For the 12-degree polynomial, the relative pixel sensitivities are normal distributions. The one-sample Kolmogorov-Smirnov test confirms that both distributions, for polynomial degrees >4, in FIGS. 5C and 5D pass the normality test at ~100% confidence level. FIGS. 5C and 5D show the effect of the order of the polynomial surface model on the pixel sensitivity distribution. For the 6 MV flattened beam, each successive polynomial narrows the sensitivity distributions as they become more normally distributed. For the 6MV FFF beam the $2^{nd}$ and $3^{rd}$ degree polynomials are clearly inadequate, but there is little difference between the $4^{th}$ and $50^{th}$ degree fits. These findings are expected due to the inherent symmetrical nature of the lower-degree polynomials and the limitation in feature capturing of the EPID's signal that has various local characteristics due to the energy fluence backscattering by the underlying EPID's metal components. At slightly higher degree of the fitting polynomials, the models capture all fluence-signal features, leaving out the pixel-to-pixel variations of the PSM.

PSM Energy Independence

Figure 6A:
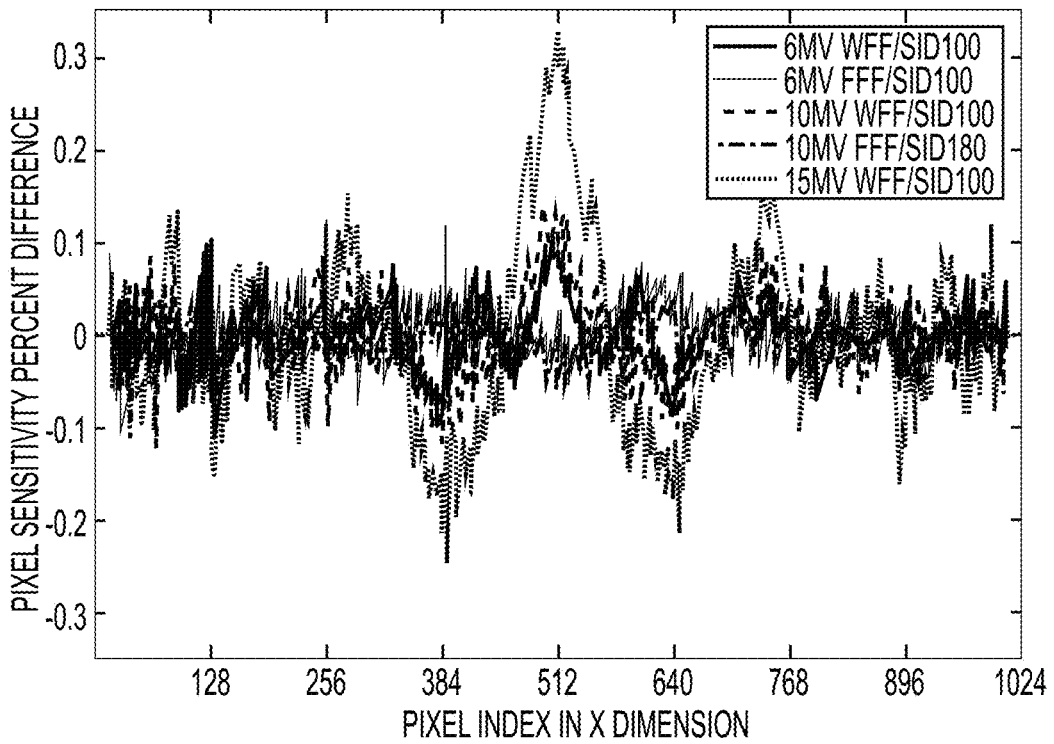
FIG. 6A is a X profile of the percent difference of PSMs for different configurations and the PSM shown in FIG. 5B.
Figure 6B:
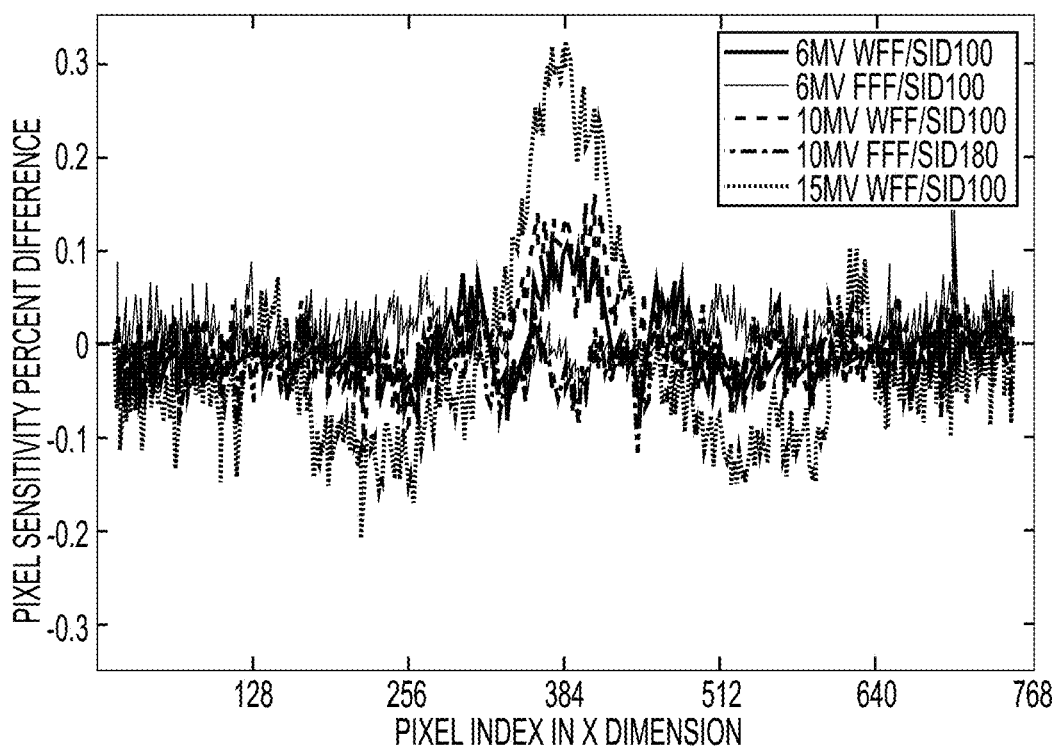
FIG. 6B is a Y profile of the percent difference of PSMs for different configurations and the PSM shown in FIG. 5B.
Figure 6C:
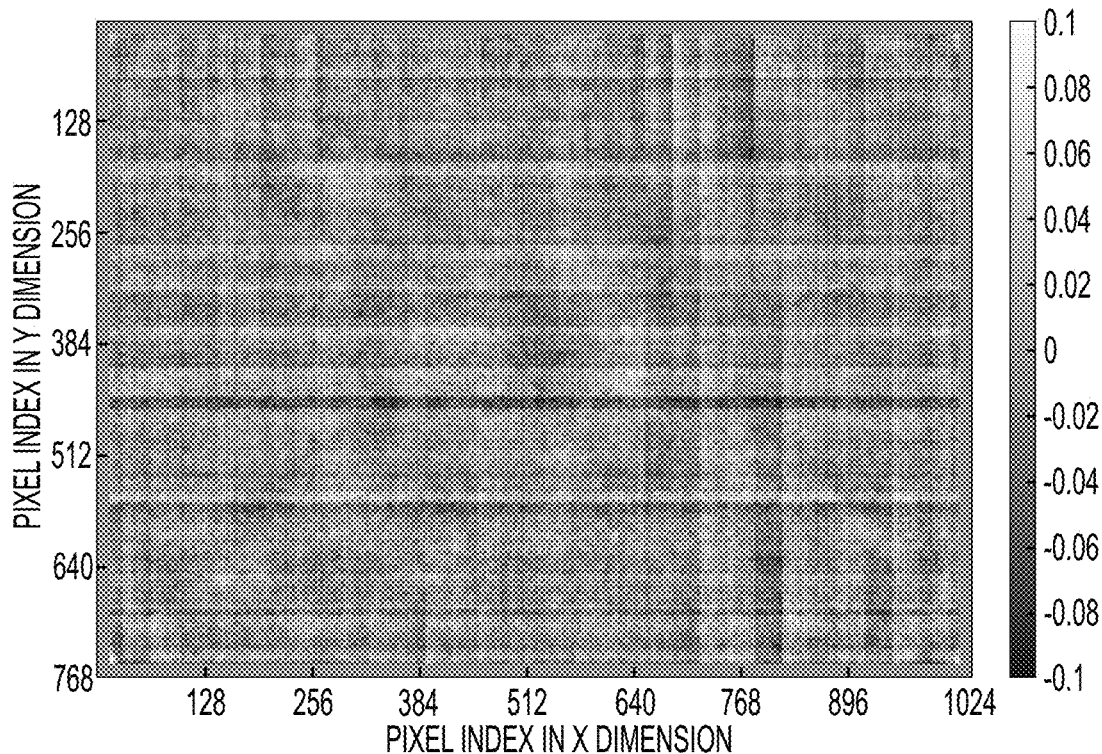
FIG. 6C is a percent difference image between PSMs generated with 6MV FFF beam and 10MV FFF beam, both measured at SID=180 cm.

The PSM beam energy dependence/independence can be illustrated by evaluating the pixel-by-pixel percent difference between the PSM in FIG. 5B and PSMs generated with different beam configurations using the formula $100\times(1-PSM/PSM_{ref})$. Profiles through the percent difference maps are given in FIGS. 6A and 6B. FIG. 6A is a X profile of the percent difference of PSMs for different configurations and the PSM shown in FIG. 5B. FIG. 6B is a Y profile of the percent difference of PSMs for different configurations and the PSM shown in FIG. 5B. The PSM percent-difference profiles for the flattened 6, 10 and 15 MV beams show fast-varying features that were largely cancelled out, leaving only slow-varying features which show the inexactness of capturing the underlying fluence-signal. On the other hand, the profiles of the 6 and 10 MV FFF PSMs are reproducible within ≤0.1% as emphasized by the 2D difference image in FIG. 6C. FIG. 6C is a percent difference image between PSMs generated with 6MV FFF beam and 10MV FFF beam, both measured at SID=180 cm. FIG. 6C shows that PSMs generated with flattening filter free (FFF) beams are indistinguishable within ~0.1%. All measurements occurred at SID equal to 100 cm, except the reference profile, in FIG. 5B, and the 10MV FFF profile were measured at SID=180 cm. The optimal modeled PSMs, calculated for all commissioned energy beams, are practically indistinguishable; the mean and standard deviation of the mean, max, min and standard deviation sensitivity values, between the 0.1 and the 99.9 percentiles, are 1.0±0.0, 1.033±0.001, 0.980±0.002, and 0.0064±0.0003, respectively. In addition, the mean and standard deviation of the first, second, and infinity norms are 962±52, 1.47±0.08, and 0.026±0.004, respectively. The results show that the FFF generated PSMs show the same trends, as do the WFF PSMs.

Figure 7A:
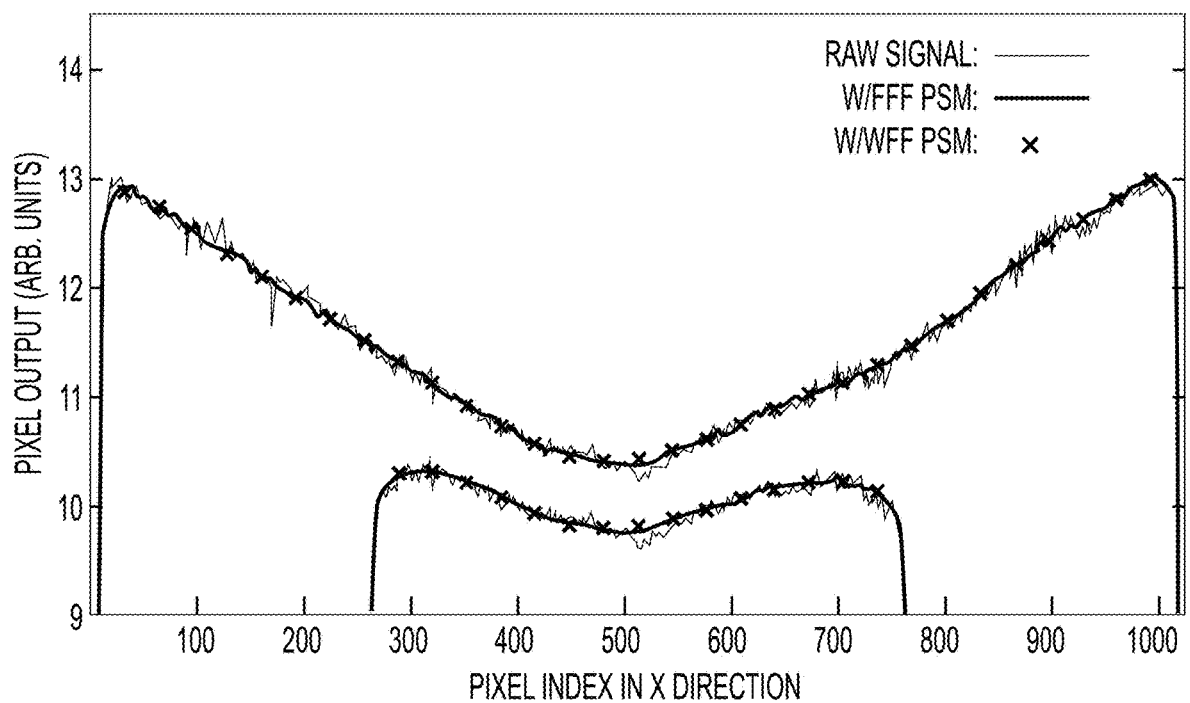
FIGS. 7A & 7B show raw and PSM-corrected profiles through the center of the EPID for the 6 MV flattened beam measured at SID=100 cm in the X and Y directions, respectively.
Figure 7B:
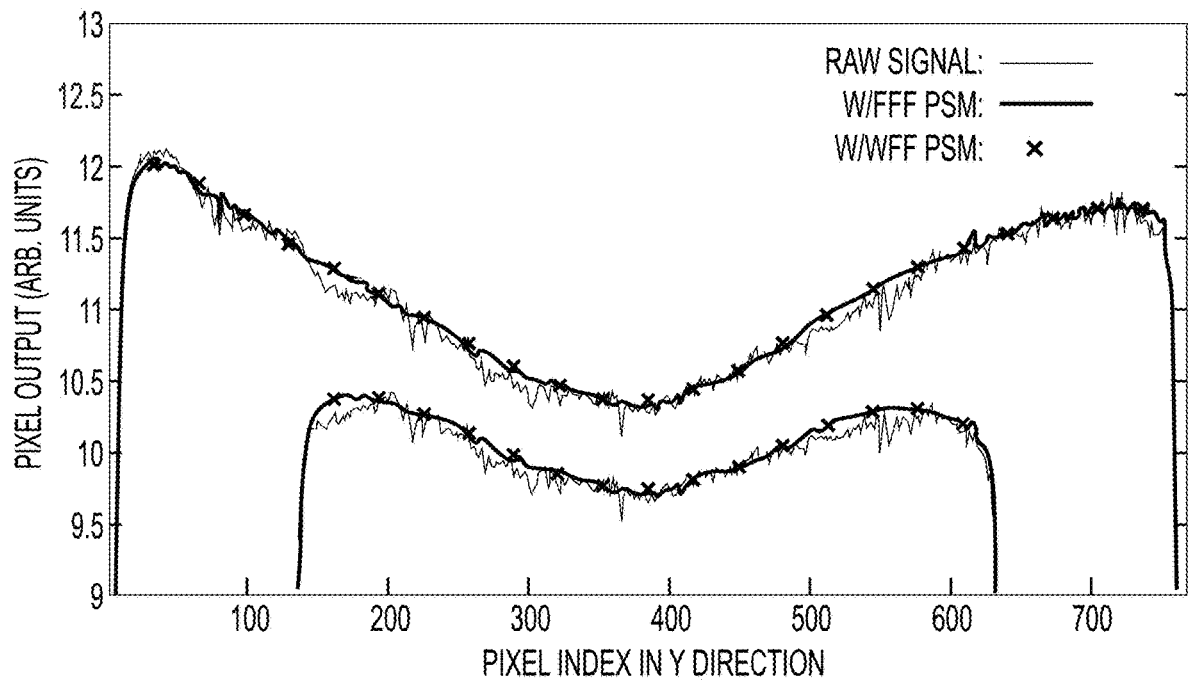

While the flattened and FFF beams separately indicate PSM energy-independence, together they show 0.3% differences near the imager center/beam central axis as shown in FIG. 5E. To investigate this difference, an inter-comparison is performed of 6MV open field measurements acquired at SID equal to 100 cm prior and subsequent to pixels correction with a PSM generated by the same signal and the FFF-generated PSM in FIGS. 7A and 7B. FIGS. 7A & 7B show raw and PSM-corrected profiles through the center of the EPID for the 6 MV flattened beam measured at SID=100 cm in the X and Y directions, respectively for 40×30 and 20×20 $cm^2$ fields. The high frequency signal shows the raw EPID signals, the low frequency signal shows the signals corrected with the PSM generated with the 6 MV FFF beam measured at SID=180 cm. The "x" markers show a sparse sampling of the signals corrected with the PSM generated with the 6 MV flattened beam at SID=100 cm. The signals, corrected with 6 MV FFF PSM, reproduce the smooth fluence-signal, and illustrate energy independence. The profiles corrected with the FFF PSM reproduce the fluence-signal and maintain the flattened beams output, horns, and fall off. The symmetry of the raw fields in the x-direction and the rise in the EPID signal due to the backscattering in the y-profiles can be easily identified when correcting the raw signal using both PSMs indistinctly. Similar results are obtained for 10 and 15 MV flattened beam measurements when corrected with PSM generated with FFF beams. Considering the PSMs measured by the 15 different beam configurations as independent measures of the same quantity, statistical analyses find that the average pixel-wise precision is ~0.45% and the maximum pixel-wise deviation is ~0.92%. The difference in PSMs generated by flattened and FFF beams in addition to the impact of SID on the PSM is elaborated upon in later sections of the present disclosure.

Output Position-Invariance Validation

Figure 8A:
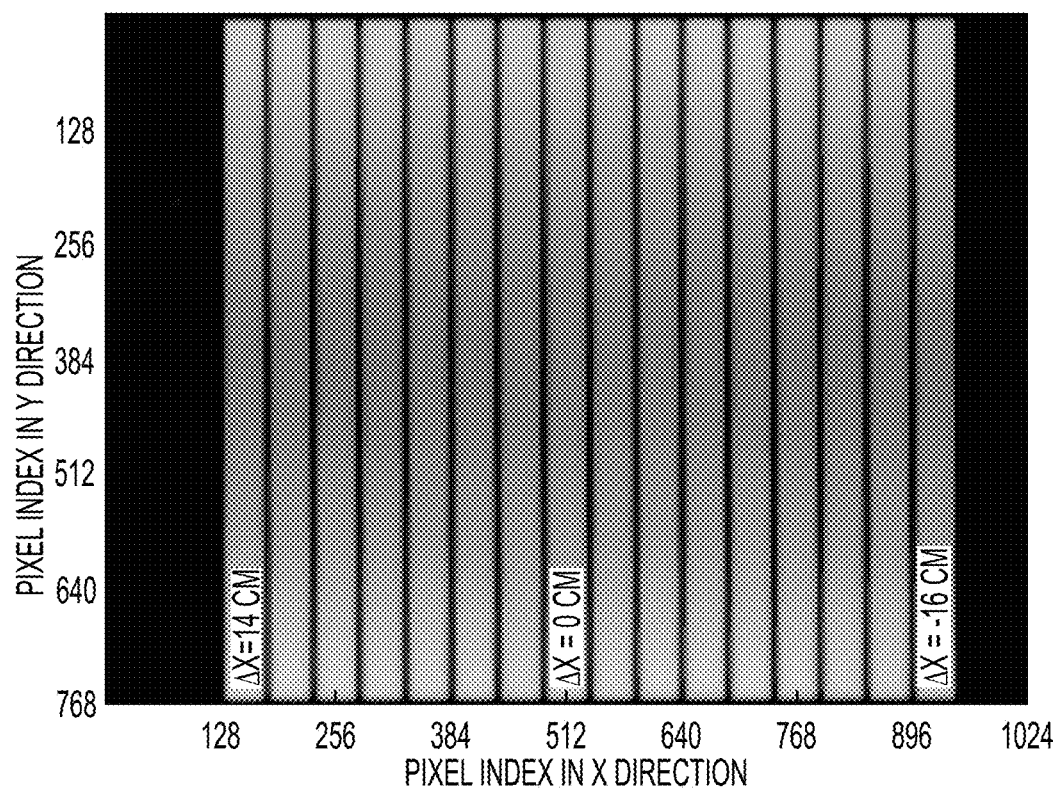
FIGS. 8A & 8B show overlays of PSM-corrected 6 MV measurements.
Figure 8B:
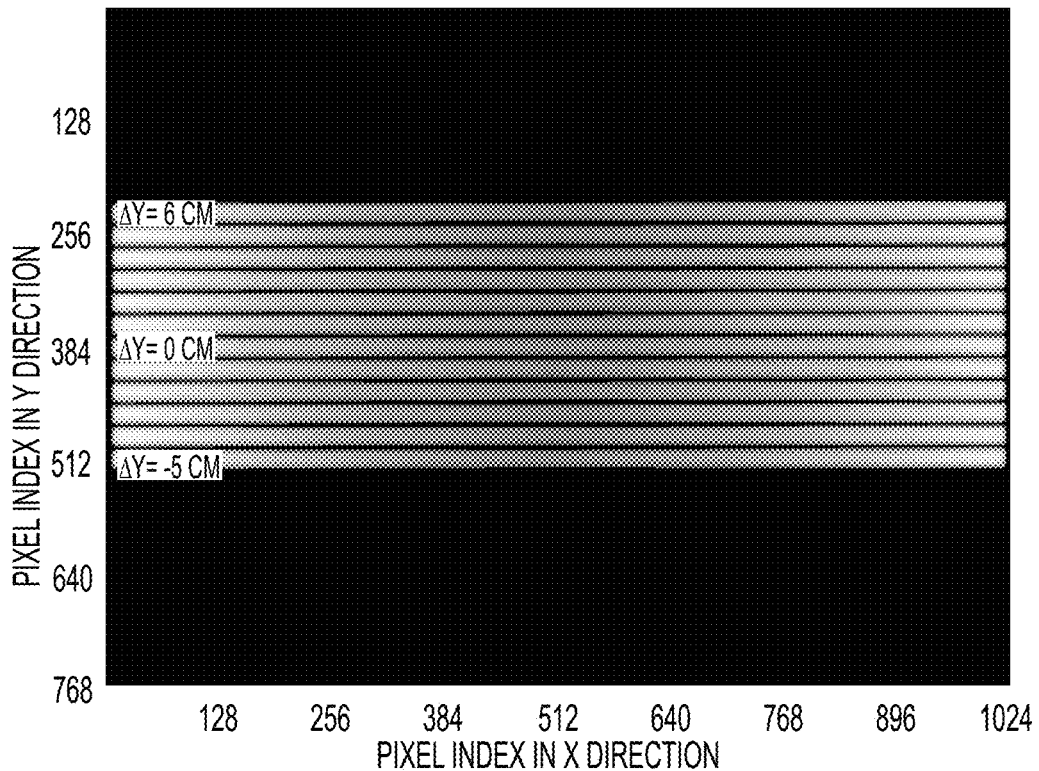
Figure 8C:
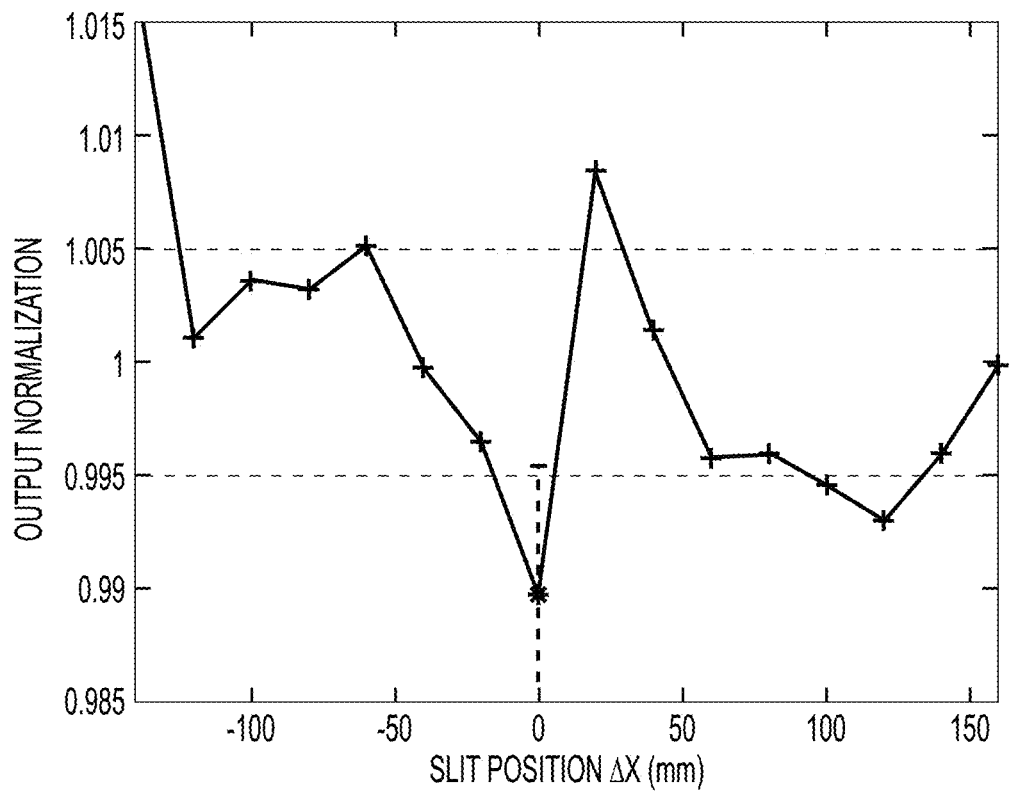
FIGS. 8C & 8D show the relative output from the x and y profiles, respectively.
Figure 8D:
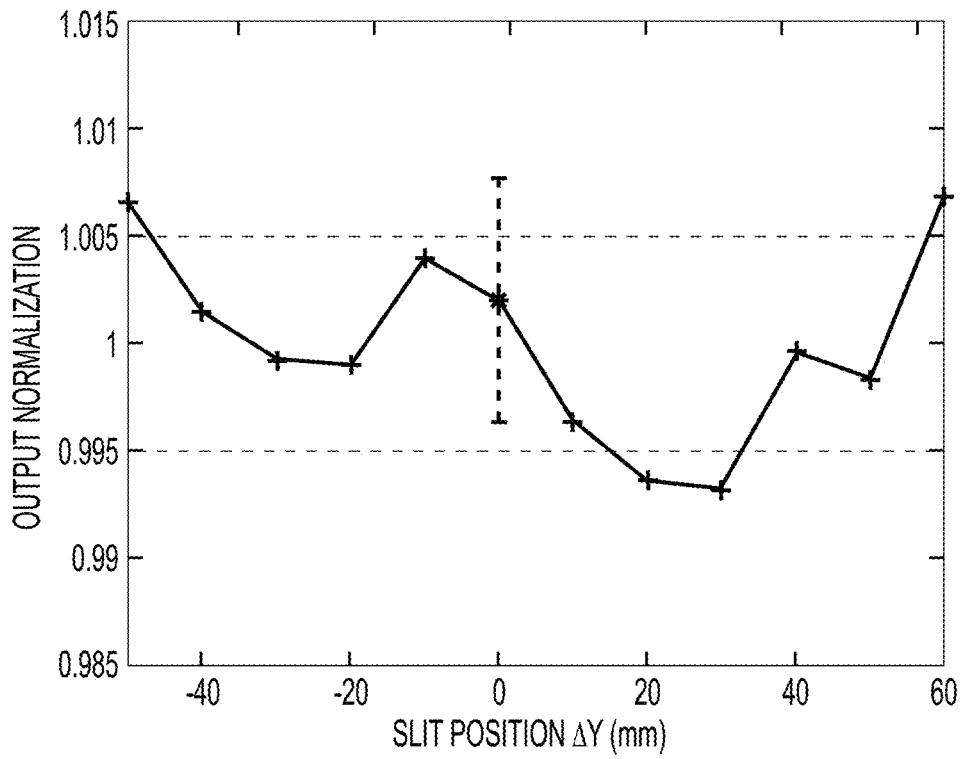

FIGS. 8A and 8B show overlays the measurements of the x and y-slit position-invariance output validation. FIGS. 8A & 8B show overlays of PSM-corrected 6 MV measurements. During the delivery of the x-slits, the EPID maximum and minimum displacements were 15 cm in the positive x-direction and 16 cm in the negative x-direction. While, at the delivery of the y-slits, the maximum and the minimum displacements for the EPID panel were 6 cm and 7 cm in the positive (couch) and negative (gantry) y directions, respectively. Each image was corrected for background dark-field, pixel defect map and the 6 MV FFF pixels sensitivity map shown in FIG. 5B. For each slit in FIGS. 8A and 8B, the delivery was 250 MU with a 6 MV beam with flattening filter with the measurement SID equal to 100 cm. The output of each radiation slit is computed as the sum of all pixel values within the central 80% of the slit field size in the x and y directions to reduce slit alignment/beam fall off affects. The output is then normalized by the mean output of all slits and shown in FIGS. 8C and 8D. FIGS. 8C and 8D show the relative output from the x and y profiles, respectively. The error bars, i.e., 0.57%, emphasize the standard deviation in measured outputs, within same session, by EPID model aS1000. The relative output variations, shown in FIGS. 8C and 8D, are mostly within ±0.5%, which is indicated by the dashed lines. The residual output variation in FIGS. 8C and 8D also includes components from the PSM, machine output variations, background removal and the EPID measurement reproducibility. The error bars, at slit indices equal to 0, show the standard deviations in outputs of radiation deliveries for flood field EPID signals. A cine sequence of EPID images (i.e., 944 frames delivered in same session) for 6MV beam with flattening filter measured at SID equal to 100 cm were used to estimate the error bars. The error bar data were background-corrected only (i.e., neither PSM nor pixel defect map were applied). The standard deviation was minimized through integration of n consecutive images, where n=1 to 100, to eliminate variations due to the periodic banding artifacts.

The measured outputs are self-consistent within the beam delivery variation of ~0.57%. The pixel-by-pixel evaluation of the relative standard deviation finds that 66% (1-std deviation) are within 0.76% for the irradiations of FIGS. 8A and 8B, indicating consistency between the slit measurements and presently disclosed PSM within 0.76%.

PSM Stability

The EPID PSM is robust to local changes in pixels sensitivity over time. For 6 MV flattened beam, the cross-correlation coefficient is 0.9995 between pixel sensitivity maps generated on images acquired 3 months apart. The max, min, mean and standard deviation of the percent difference between the two PSMs, were 0.66%, −0.39%, 0.01%, and 0.07%, respectively. In short, the PSM is stable enough for long-term absolute EPID dosimetry and insensitive to local damage to the EPID or its associated electronics.

An approach to compute the PSM of the MV EPID detector is discussed above using a model which utilizes the fundamental features of MV radiation from linacs; the underlying energy fluence is smooth and somewhat symmetric. Here, surface-fit polynomials are used to measured EPID flood fields to ascertain the underlying smooth fluence-signal and extract the PSM. The PSM generation does not require lateral shifts of the detector array utilized by other existing methods, hence, it should be applicable to EPIDs in fixed locations with respect to the linac head. Within fitting errors, the PSM is independent of the incident photon energy fluence; both flattened and FFF beams were tested. Changing the SID changed the position of the incident energy fluence on the imager (with the energy fluence broadening with increasing SID), but did not change the generated PSM. Because the PSM is energy independent, it can be used to correct through-phantom/patient EPID signals without any further pixel response modification.

The PSM accounts for the relative changes in screen response, individual pixel size (i.e., ability to capture light photons from the screen and the direct photon interactions in the photo diode) and the detector read-out electronics. Monte Carlo simulations show that EPID energy deposition kernels from mono-energetic photons vary in width and integral energy deposition, indicating that the absolute response of the imager per photon is energy dependent. For FFF beams, the energy spectrum is nearly constant across the beam, thus, per irradiation, the pixel energy dependent response is position-invariant. As the beam energy increases from 6 MV FFF to 10 MV FFF, this beam-specific, absolute pixel response will decrease. For flattened beams, the energy spectrum is hardened on the beam central axis compared with the beam periphery. Therefore, the relative energy dependent response aspects will be a radial symmetric component whose magnitude is dictated by the differential energy response of the screen/pixel from the hardest part of the photon spectrum (the beam central axis) to the softest part of the photon spectrum (the beam periphery where the flattening filter is thinnest). The measured PSM independence (within ~0.5%) suggests that differential energy variations across each flattened or FFF beam have a negligible effect on the relative pixel response. Indeed, it has been shown that above 2 MeV, integral kernel energy deposition varies by $1 \times 10^{-4}$ per MeV, confirming the low differential energy dependence. Hence, while the absolute pixel response changes between beam configurations, the changes are nearly constant across the PSM, which is a measure of relative pixel response.

When both WFF and FFF beams are available on a linac, the premise that simple models are preferred over complex ones suggests that FFF are preferred for PSM acquisition. FFF beams have a simple convex surface for which $n \geq 5$ degree polynomial produce a high quality surface fit, while WFF beams may have a central bump and horns, for which $n \geq 12$ degree polynomial is required for a quality fit. The profile features of FIGS. 6A and 6B show that for flattened or for FFF beams, PSM slow-varying components are indistinct within ~0.5% and the fast-varying components are indistinct within ~0.1%. Similarly, when multiple SIDs are available, larger SIDs are preferred as they broaden the slow-varying fluence-signal. Direct comparison of 6 MV FFF generated PSMs at different 100 and 180 cm SIDs show <0.1% differences (FIGS. 6A and 6B). Overall, it was found that PSMs generated with FFF beams at the largest SID available for the EPID yield the highest quality fit.

On the other hand, for flattened beams, the in-air energy fluence surface has horn/spindle-like toroid features which are difficult to capture in fitting even with relatively high order polynomial terms. Moreover, due to the symmetry and the relative number of pixels, the edges pixels dominate the fit compared to the fit at the central region, resulting in a poorer fit near the beam central axis harder for flattened beams. Like the FFF beam, increasing the SID reduces energy fluence gradient, improving the surface fit and PSM, however, additional steps can be taken to further improve the PSM quality. For example, slab or custom shaped attenuators would reduce the beam horns and likely improve the quality of the surface fit. Special mathematical models may be developed for specific attenuators such that it best captures the fluence-signal features and leaves out diode detectors variations. When surface fitting is utilized, the fit quality should be confirmed by cross-checking raw and fitted profiles and/or residuals from the fitting to verify that the surface fit reproduced the features of the underlying fluence.

Polynomial-based surface fitting is used in various examples to determine the shape of the underlying fluence-signal due to its intuitive simplicity. However, other surface fitting, regional-surface fitting, weighted-surface fitting, signal smoothing, low-pass filtering, or signal frequency decomposition methods may also work for determining the underlying fluence-signal. As the polynomial surface fitting yields an acceptable PSM, i.e., PSM that preserve fluence-signal features and does not alter the local signal patches, inter-comparison of alternative fluence-signal determination methods outside the scope of this study can be considered. Such methods may be beneficial when highly accurate PSMs are required and FFF-beams are not available.

It was found that the PSM was stable at the <1% level for measurements separated by 3 months. In contrast to prior approaches to determining PSM that found energy/modality dependence for the PSM, it was found that using the method(s) according to some aspects described herein, the PSM is energy/modality independent for photons. A possible reason for this is that prior approaches for determining PSM did not separate the imager backscatter signal from the PSM, while the PSM determined herein excludes the backscatter signal which varies as a function of energy.

Computationally, method(s) according to some aspects described herein excludes backscatter from the PSM because the non-uniform backscatter results in a slowly varying signal for the open field irradiations used in determining the PSM. For example, at 6 MV, the backscattered signal may be modeled as ~14 cm FWHM Gaussian distribution. This low frequency signal component is captured by the fluence-fitting polynomials and excluded from the PSM. From a physics standpoint, the present method excludes backscatter since it is induced by the incident energy fluence, thus, backscatter is part of the overall fluence signal. For PSMs that exclude backscatter, calculations to be compared with PSM corrected EPID measurements need to account for backscatter signal components in the calculational model. Such inclusion has been accomplished with analytic and Monte Carlo-based EPID calculation modules, which can then account for the changing backscatter location as a function of imager position.

Because method(s) according to some aspects described herein considers all low-frequency components of the signal to be fluence-induced, the method(s) are susceptible to non-fluence induced low frequency signal perturbations. For example, if the EPID screen had a linear decrease in light output response along in the x-direction, the low-frequency fit would capture that change in response, erroneously attributing the slope to the fluence-signal, not the pixel sensitivity map. Hence, the PSM-corrected signal would show a linear tilt in the x-direction. Because of this possibility, there may not be absolute PSM accuracy using method(s) according to some aspects described herein. However, accuracy can be assessed by comparing the consistency of the corrected EPID signal with respect to other measurement methods as has been done by others. Here, the accuracy with respect to a series of shifted panel measurements are bounded, finding consistency within the 0.76%. For imagers in a fixed geometry, accuracy can be established by comparison with an independent dosimetry system, such as a scanning detector, detector array, or film, with e.g. Monte Carlo calculations of the ratio between the verification dosimeter and the EPID to account for differences in the detector systems inherent energy response. The 0.76% PSM accuracy is limited by the inherent uncertainties in the slit measurements used to establish the accuracy. The PSM precision is ~0.45%. With this accuracy and precision, PSMs determined with method(s) according to some aspects described herein should be adequate for many clinical tasks. However, as different clinical tasks have different tolerance limits, the physicist should ensure the post-PSM-applied measurand accuracy and precision is adequate for each particular clinical task.

Compared with prior work, method(s) according to some aspects described herein do not require multiple measurements while shifting the imager beneath a fixed radiation field. Since most shifting methods rely on overlapping features to derive the PSM, non-overlap regions (near the imager boundary) do not have accurate values. The method(s) according to some aspects described herein are not subject to this limitation. The build-up of error in detector calibration factors inherent to shift-based techniques has been reported with other detector systems. For 2-D diode array calibration, it was found that 0.3% linac symmetry variations between measurements led to up to 1.2% calibration errors. For a 251 ion chamber array, it has been found that 0.1% beam shape perturbations can lead to 2% calibration errors. In such instances, error build-up is inherent to shifting techniques and that the error propagation is proportional to the number of detection channels. The root causes of the error-buildup are differences in beam output, beam profile, pixel sensitivity, and scatter conditions between successive irradiations.

To quantify the PSM error propagation inherent to the shifting method for aS1000 EPID, simplistic simulations were conducted to determine the effects of offset errors, machine output variation, and signal ghosting. The simulation began with an assumed underlying smooth 6 MV flattened beam image and an assumed PSM with 3% pixel-to-pixel variance. Simulations mimicked measurements with the addition of the aforementioned variations, reconstructed the PSM from those measurements, then compared the assumed and reconstructed PSMs. It was found that single pixel misalignment in the imager shift would result in ≥1% PSM deviations in 6% of the EPID panel pixels; a 0.1% machine output variation between measurements would result in up-to 5% pixel sensitivity errors; and that a 0.1% background offset (mimicking ghosting) could result in 25% errors in 85% of EPID pixels. Prior approaches utilized sequential calibration field and dark-field irradiations to minimize the effect of the ~1% image ghosting and small (1 cm) imager offsets to minimize the change in scatter conditions inherent to the aS1000 imager (which has non-uniform backscatter).

While the simulation confirmed the error build-up inherent to the shifting methods (specifically, methods referenced in this work), image pre-processing and/or smoothing of prior work by others was not performed. It has been noted that the need to manipulate the PSM map to reduce the noise and the discontinuities at the junction of the shifting segments, while some others applied an un-described smoothing filter on the images prior to computing the PSM. These steps may be helpful to suppress errors propagation in the shifting method. However, intuitively, such manipulations increase the correlations between neighboring pixels response. By combining smoothing and shifting, perturbation of singular EPID pixel affects the full EPID surface. It has been discovered herein through the experimenting that un-masked errors (bad-pixel regions) propagate from a damaged location on the EPID to remote readings when a shifting method is used to generate the PSM. On the other hand, with method(s) according to some aspects described herein, the impact of a dead region on the EPID detector array is either readily detected, or remains local. Moreover, in a region of the signal discontinuity, due to damaged pixel diode detectors, a low order polynomial fit is unable to provide a good fit, making for easy detection of the bad pixel region. Unless a substantial continuous area of the EPID is defective, method(s) according to some aspects described herein are very robust to dead pixels in a way that protects the underlying signal, not the bad individual pixel readings.

The 1.39% range of PSM pixel calibration factors that is observed, i.e, the FWHM of FIGS. 5C and 5D, are similar to published residual variations. It has been reported that dose variability with detector displacement was reduced to <1% post PSM correction. Some prior PSM validation relied on intercomparing profiles from different "matched" linacs, finding 1-2% differences acceptable and 1-D 1.5%/1.5 mm gamma passing rates of >92% for photons. The differences in method(s) according to some aspects described herein are less than this level.

Presented herein is an approach to generate the pixel sensitivity map for the MV electronic portal imaging devices of linear accelerators. The method(s) according to some aspects described herein do not require shifting the imager, therefore is applicable for EPIDs in a fixed geometry with respect to the treatment head. the method(s) according to some aspects described herein are premised upon the fact that the energy fluence output from MV beams is smooth with low gradients. Therefore, the raw measured EPID signal can be decomposed into a smooth surface produced by the unattenuated and/or attenuated incident radiation and a high frequency component which is due to pixel-to-pixel response sensitivity variations. In some examples, up to $12^{th}$ order polynomial surface fits were used to capture the low frequency component. The quality of a resultant PSMs is dependent on the quality of polynomial surface fit utilized. The most accurate PSM is found for 6 MV FFF beams measured at SID equal to 180 cm with $10^{th}$ polynomial model. Within fitting errors, the PSM is found to be independent of beam energy for 6, and 10MV FFF beams within ≤0.1%, as well as 6, 10, and 15 MV flattened beams within ≤0.24%, which makes the 6MV FFF PSM suitable for correcting both flattened and FFF EPID signals regardless of the energy.

EXAMPLES AND EXPERIMENTAL RESULTS

Practice of certain aspects of the present disclosure will be still more fully understood from the following examples and experimental results, which are presented herein for illustration only and should not be construed as limiting the present disclosure in any way.

Method and System to Determine the Dosimetric Pixel Sensitivity Matrix for Medical Imagers

DESCRIPTION

In radiation oncology, medical imagers can be used as radiation dosimeters. This requires that the pixels of the imagers be calibrated in terms of dosimetric response, which differs from the non-dosimetric flood field calibration normally used to obtain acceptable images for viewing.

Prior work on dosimetric calibration of imagers require shifting the imaging detector under a fixed radiation field, using the correlation between pixels to derive calibration factors. Drawbacks of this method are 1) it requires that the imaging panel can be moved with respect to the radiation source and 2) it is highly susceptible to errors due to uncertainties in the distance moved and errors due to variabilities in the radiation source.

In some aspects, the present disclosure proposes a new method and system in which the source and imager remain in a fixed geometry for calibration. The method(s) and system(s) according to some aspects described herein take advantage that radiation fields used for calibration are smooth surfaces with known maximum gradients. Deviations between a measured calibration image and the smooth surface are due to dosimetric pixel sensitivity variations, hence, the ratio of the surface and the calibration image is the dosimetric pixel intensity map.

From a measured image, multiple methods can be used to determine the shape of the smooth surface, including Fourier decomposition, surface fitting, and nearly any image denoising technique.

An aspect of an implementation of the present disclosure provides a system, method and computer readable medium for, among other things, a regression-based approach to compute the pixels gain map of linear accelerator portal imaging devices.

An aspect of an implementation of the present disclosure provides a system, method and computer readable medium for, among other things, determining the dosimetric pixel sensitivity matrix for medical imagers.

Regression-based Method and System to Compute the Pixels Sensitivity Map of MV Portal Imaging Devices Purpose: To determine the pixel sensitivity map (PSM) for an amorphous silicon electronic portal imaging device (EPID) using a single flood field signal.

Methods: A raw acquired EPID signal may be decomposed into the incident particle fluence signal, the inherent pixels gain, and the background signal. Particle fluence varies slowly and is locally spatially-constant. Pixel response is a fast and abrupt varying signal which perturbs the local fluence response. The background signal is due to the EPID panel electronics, and is determined during radiation absence. To determine the PSM, the background signal is first corrected for. Then, a regression model is applied that captures the underlying slowly varying features of the corrected EPID signal. The captured fluence signal is then used to decouple the PSM signal from the corrected EPID signal. To validate the generated PSM, it has been confirmed herein that an open field output is EPID-position independent and results herein are compared to prior PSM generation methods.

Results: The EPID pixel gain values are normally distributed with mean value of 1.0 and standard deviation of 0.01 for 6MV beams with and without the flattening filter. Model validation shows that a PSM, generated with this method, alters an open field output value by <1.0%. Flattening-filter free beams are found to generate PSMs which are well-described by regression models. Post PSM application, the processed signal is EPID-position independent.

Conclusion: According tom some aspect, the present disclosure provides an approach to generate the PSM for linac MV EPIDs. The method and system according to some implementations are based on the fact that the EPID signal may be decomposed into a smooth surface convolved with spatially-dependent pixels gain map. This method and system does not require shifting the EPID panel, enabling it PSM generation for linacs with fixed EPIDS, nor requires multiple EPID panel irradiations.

This approach improves EPID transit dosimetry and enables automatic EPID signal calibration.

An aspect of an implementation of the present disclosure provides a system, method and computer readable medium for, among other things, a regression-based method and system to compute the pixels sensitivity map of MV portal imaging devices.

Additional Examples

1. A method for providing) a) the dosimetric pixel sensitivity matrix for medical imagers, b) the shape of the smooth surface, including Fourier decomposition, surface fitting, and nearly any image denoising technique, or c) a regression-based approach to compute the pixels gain map of linear accelerator portal imaging devices, as described herein.

2. The method according to example 1, including each and every novel feature or combination of features disclosed herein.

3. A system for providing a) the dosimetric pixel sensitivity matrix for medical imagers, b) the shape of the smooth surface, including Fourier decomposition, surface fitting, and nearly any image denoising technique, or c) a regression-based approach to compute the pixels gain map of linear accelerator portal imaging devices, as described herein.

4. The system according to example 3, including each and every novel feature or combination of features disclosed herein.

5. A computer-readable storage medium having computer-executable instructions stored thereon which, when executed by one or more processors, cause one or more computers to perform functions for performing a) the dosimetric pixel sensitivity matrix for medical imagers, b) the shape of the smooth surface, including Fourier decomposition, surface fitting, and nearly any image denoising technique, or c) a regression-based approach to compute the pixels gain map of linear accelerator portal imaging devices, as described herein.

6. The computer-readable storage medium of claim 5, including each and every novel feature or combination of features disclosed herein.

It should be appreciated that the logical operations described herein with respect to the various figures may be implemented (1) as a sequence of computer implemented acts or program modules (i.e., software) running on a computing device (e.g., the computing device described in FIG. 9), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 9:
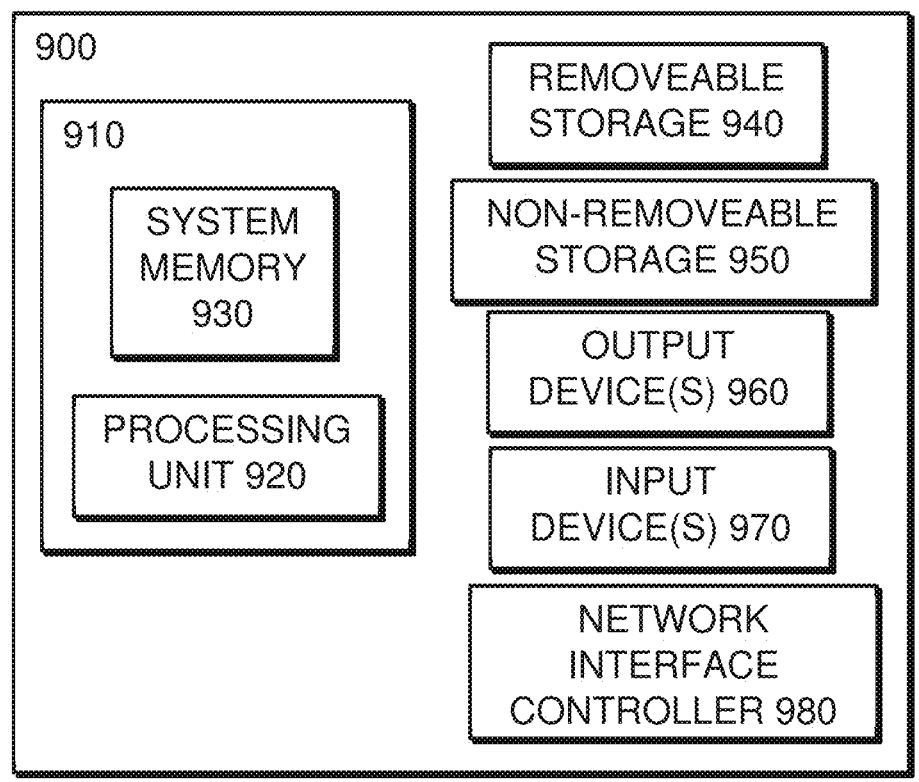
FIG. 9 illustrates an exemplary computer system suitable for implementing the several embodiments of the disclosure.

Referring to FIG. 9, an example computing device 900 upon which embodiments of the present disclosure may be implemented is illustrated. For example, the controller 108 described herein may be implemented as a computing device, such as computing device 900. It should be understood that the example computing device 900 is only one example of a suitable computing environment upon which embodiments of the present disclosure may be implemented. Optionally, the computing device 900 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In an embodiment of the present disclosure, the computing device 900 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computing device 900 to provide the functionality of a number of servers that is not directly bound to the number of computers in the computing device 900. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In its most basic configuration, computing device 900 typically includes at least one processing unit 920 and system memory 930. Depending on the exact configuration and type of computing device, system memory 930 may be volatile (such as random access memory (RAM)), non-volatile (such as read-only memory (ROM), flash memory, etc.), or some combination of the two. This most basic configuration is illustrated in FIG. 9 by dashed line 910. The processing unit 920 may be a standard programmable processor that performs arithmetic and logic operations necessary for operation of the computing device 900. While only one processing unit 920 is shown, multiple processors may be present. Thus, while instructions may be discussed as executed by a processor, the instructions may be executed simultaneously, serially, or otherwise executed by one or multiple processors. The computing device 900 may also include a bus or other communication mechanism for communicating information among various components of the computing device 900.

Computing device 900 may have additional features/functionality. For example, computing device 900 may include additional storage such as removable storage 940 and non-removable storage 950 including, but not limited to, magnetic or optical disks or tapes. Computing device 900 may also contain network connection(s) 980 that allow the device to communicate with other devices such as over the communication pathways described herein. The network connection(s) 980 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. Computing device 900 may also have input device(s) 970 such as a keyboards, keypads, switches, dials, mice, track balls, touch screens, voice recognizers, card readers, paper tape readers, or other well-known input devices. Output device(s) 960 such as a printers, video monitors, liquid crystal displays (LCDs), touch screen displays, displays, speakers, etc. may also be included. The additional devices may be connected to the bus in order to facilitate communication of data among the components of the computing device 900. All these devices are well known in the art and need not be discussed at length here.

The processing unit 920 may be configured to execute program code encoded in tangible, computer-readable media. Tangible, computer-readable media refers to any media that is capable of providing data that causes the computing device 900 (i.e., a machine) to operate in a particular fashion. Various computer-readable media may be utilized to provide instructions to the processing unit 920 for execution. Example tangible, computer-readable media may include, but is not limited to, volatile media, non-volatile media, removable media and non-removable media implemented in any method or technology for storage of information such as computer readable instructions, data structures, program modules or other data. System memory 930, removable storage 940, and non-removable storage 950 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

In an example implementation, the processing unit 920 may execute program code stored in the system memory 930. For example, the bus may carry data to the system memory 930, from which the processing unit 920 receives and executes instructions. The data received by the system memory 930 may optionally be stored on the removable storage 940 or the non-removable storage 950 before or after execution by the processing unit 920.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Embodiments of the methods and systems may be described herein with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. An image calibration method, comprising:
receiving a flood field signal captured with an image detector from incident energy fluence produced by a signal source;
receiving a model that describes topological properties of the incident energy fluence on the image detector; and
generating a fluence-signal-fitted model of the incident energy fluence in the flood field signal based on the model, wherein the fluence-signal-fitted model includes separated frequency components of the flood field signal that are characteristic of variations in the incident energy fluence.

2. The image calibration method of claim 1, wherein the model describes a known maximum in-field energy fluence gradient of the incident energy fluence.

3. The image calibration method of claim 1, wherein the model describes a known frequency cut-off for variations in the incident energy fluence.

4. The image calibration method of claim 1, wherein the separated frequency components are at or below a known maximum in-field energy fluence gradient.

5. The image calibration method of claim 1, wherein the flood field signal includes both frequency components that are characteristic of the incident energy fluence and frequency components characteristic of pixel-to-pixel sensitivity variations of the image detector.

6. The image calibration method of claim 1, further comprising:
correcting the flood field signal for background dark-field and/or bad pixels to produce a corrected image signal.

7. The image calibration method of claim 6, further comprising:
determining a pixel sensitivity matrix from the flood field signal and the fluence-signal-fitted model.

8. The image calibration method of claim 7, wherein determining the pixel sensitivity matrix comprises adjusting the corrected image signal based on the fluence-signal-fitted model.

9. The image calibration method of claim 8, wherein adjusting the corrected image signal based on the fluence-signal-fitted model comprises scaling the corrected image signal by the fluence-signal-fitted model or subtracting the fluence-signal-fitted model from the corrected image.

10. The image calibration method of claim 7, further comprising:
capturing an image with the image detector of an object irradiated by energy fluence produced by the signal source; and
correcting the image of the object using the pixel sensitivity matrix.

11. An image calibration method, comprising:
receiving a fluence-signal-fitted model of incident energy fluence produced by a signal source that is captured in a flood field signal by an image detector, wherein the fluence-signal-fitted model includes separated frequency components of the flood field signal that are characteristic of variations in the incident energy fluence; and
generating a pixel sensitivity map of the image detector by adjusting the flood field signal based on the fluence-signal-fitted model.

12. The image calibration method of claim 11, wherein the flood field signal is a corrected image signal that is corrected for background dark-field and/or bad pixels of the image detector.

13. The image calibration method of claim 11, wherein the flood field signal includes both frequency components that are characteristic of the incident energy fluence and frequency components characteristic of pixel-to-pixel sensitivity variations of the image detector.

14. The image calibration method of claim 11, wherein the fluence-signal-fitted model has a frequency cut-off characteristic of topological properties of the incident energy fluence.

15. The image calibration method of claim 11, wherein adjusting the flood field signal based on the fluence-signal-fitted model comprises scaling the flood field signal by the fluence-signal-fitted model or subtracting the fluence-signal-fitted model from the flood field signal.

16. The image calibration method of claim 11, further comprising:
capturing an image with the image detector of an object irradiated by energy fluence produced by the signal source; and
correcting the image of the object using the pixel sensitivity map.

17. The image calibration method of claim 11, wherein the fluence-signal-fitted model is generated based on a model that describes topological properties of the incident energy fluence produced by the signal source.

18. The image calibration method of claim 17, wherein the model describes a known maximum in-field energy fluence gradient of the incident energy fluence.

19. The image calibration method of claim 17, wherein the model describes a known frequency cut-off for variations in the incident energy fluence.

20. The image calibration method of claim 17, wherein the separated frequency components are at or below a known maximum in-field energy fluence gradient.

* * * * *